(12) United States Patent
Stray et al.

(10) Patent No.: US 10,894,976 B2
(45) Date of Patent: Jan. 19, 2021

(54) COMPOSITIONS, METHODS, AND KITS FOR ISOLATING NUCLEIC ACIDS

(71) Applicant: Natera, Inc., San Carlos, CA (US)

(72) Inventors: James Stray, San Mateo, CA (US); Jason Tong, San Carlos, CA (US); Xiaoke Wang, San Mateo, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

(21) Appl. No.: 15/898,080

(22) Filed: Feb. 15, 2018

(65) Prior Publication Data

US 2018/0237841 A1  Aug. 23, 2018

Related U.S. Application Data

(60) Provisional application No. 62/461,735, filed on Feb. 21, 2017.

(51) Int. Cl.
*C12Q 1/6834* (2018.01)
*C12N 15/10* (2006.01)

(52) U.S. Cl.
CPC ....... *C12Q 1/6834* (2013.01); *C12N 15/1006* (2013.01)

(58) Field of Classification Search
CPC .................. C12Q 1/6834; C12N 15/1006
See application file for complete search history.

(56) References Cited

U.S. PATENT DOCUMENTS

| | | | |
|---|---|---|---|
| 3,520,488 A * | 7/1970 | Vouthier | A01K 89/01083 242/232 |
| 5,635,366 A | 6/1997 | Cooke et al. | |
| 5,716,776 A | 2/1998 | Bogart | |
| 5,753,467 A | 5/1998 | Jensen et al. | |
| 5,824,467 A | 10/1998 | Mascarenhas | |
| 5,860,917 A | 1/1999 | Comanor et al. | |
| 5,972,602 A | 11/1999 | Hyland et al. | |
| 5,994,148 A | 11/1999 | Stewart et al. | |
| 6,001,611 A | 12/1999 | Will | |
| 6,025,128 A | 2/2000 | Veltri et al. | |
| 6,066,454 A | 5/2000 | Lipshutz et al. | |
| 6,100,029 A | 8/2000 | Lapidus et al. | |
| 6,108,635 A | 8/2000 | Herren et al. | |
| 6,143,496 A | 11/2000 | Brown et al. | |
| 6,180,349 B1 | 1/2001 | Ginzinger | |
| 6,214,558 B1 | 4/2001 | Shuber et al. | |
| 6,258,540 B1 | 7/2001 | Lo et al. | |
| 6,300,077 B1 | 10/2001 | Shuber et al. | |
| 6,440,706 B1 | 8/2002 | Vogelstein et al. | |
| 6,479,235 B1 | 11/2002 | Schumm et al. | |
| 6,489,135 B1 | 12/2002 | Parrott et al. | |
| 6,720,140 B1 | 4/2004 | Hartley et al. | |
| 6,794,140 B1 * | 9/2004 | Goldsborough | C07H 21/00 435/6.1 |
| 6,807,491 B2 | 10/2004 | Pavlovic et al. | |
| 6,852,487 B1 | 10/2005 | Barany et al. | |
| 6,958,211 B2 | 10/2005 | Vingerhoets et al. | |
| 6,964,847 B1 | 11/2005 | Englert | |
| 7,035,739 B2 | 4/2006 | Schadt et al. | |
| 7,058,517 B1 | 6/2006 | Denton et al. | |
| 7,058,616 B1 | 6/2006 | Larder et al. | |
| 7,218,764 B2 | 5/2007 | Vaisberg et al. | |
| 7,297,485 B2 | 11/2007 | Bornarth et al. | |
| 7,332,277 B2 | 2/2008 | Dhallan | |
| 7,414,118 B1 | 8/2008 | Mullah et al. | |
| 7,442,506 B2 | 12/2008 | Dhallan | |
| 7,459,273 B2 | 12/2008 | Jones et al. | |
| 7,645,576 B2 | 1/2010 | Lo et al. | |
| 7,700,325 B2 | 4/2010 | Cantor et al. | |
| 7,718,367 B2 | 5/2010 | Lo et al. | |
| 7,718,370 B2 | 6/2010 | Dhallan | |
| 7,727,720 B2 | 9/2010 | Dhallan | |
| 7,805,282 B2 | 9/2010 | Casey | |
| 7,838,647 B2 | 11/2010 | Hahn et al. | |
| 7,888,017 B2 | 8/2011 | Quake | |
| 8,008,018 B2 | 9/2011 | Quake et al. | |
| 8,024,128 B2 | 9/2011 | Rabinowitz | |

(Continued)

FOREIGN PATENT DOCUMENTS

| | | |
|---|---|---|
| CN | 1650032 A | 8/2005 |
| CN | 101675169 A | 3/2010 |

(Continued)

OTHER PUBLICATIONS

Burkova et al. PLOS ONE. 2014. 9(11):e111234. (Year: 2014).*
Alaeddini, R. et al., "Forensic implications of genetic analyses from degraded DNA—A review", Forensic Science International: Genetics, vol. 4, 2010, 148-157.
Bianchi, D. W., "Circulating Fetal DNA: Its Origin and Diagnostic Potential—A Review", Placenta, vol. 25, Supplemental A, May 2004, S93-S101.
Bianchi, D. W., "Review: Fetal Cells in the Maternal Circulation: Feasibility for Prenatal Diagnosis", British Journal of Haematology, vol. 105, 1999, 574-583.
Deutsch, S. et al., "Detection of aneuploidies by paralogous sequence quantification", J Med Genet, vol. 41, 2004, 908-915.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.

(Continued)

*Primary Examiner* — Joseph G. Dauner

(57) ABSTRACT

Disclosed here is a composition for isolating nucleic acids from a biological sample, comprising a chaotropic compound and a solvent, wherein the solvent comprises a nitrile compound, tetrahydrofuran, or a combination thereof. Also disclosed is a method for binding nucleic acids to a matrix, comprising: contacting the nucleic acids from a biological sample with the matrix in the presence of a chaotropic compound and a solvent, wherein the solvent comprises a nitrile compound, tetrahydrofuran, or a combination thereof, thereby binding the nucleic acids to the matrix. Further disclosed is a kit for isolating nucleic acids from a biological sample comprising a binding buffer, wherein the binding buffer comprises a chaotropic compound and a solvent, wherein the solvent comprises a nitrile compound, tetrahydrofuran, or a combination thereof.

17 Claims, 12 Drawing Sheets

(56) References Cited

U.S. PATENT DOCUMENTS

| | | |
|---|---|---|
| 8,137,912 B2 | 3/2012 | Kapur et al. |
| 8,168,389 B2 | 5/2012 | Shoemaker et al. |
| 8,173,370 B2 | 5/2012 | Oeth et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,467,976 B2 | 8/2013 | Lo et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 9,085,798 B2 | 7/2015 | Chee |
| 9,476,095 B2 | 10/2016 | Vogelstein et al. |
| 9,487,829 B2 | 11/2016 | Vogelstein et al. |
| 9,598,731 B2 | 3/2017 | Talasaz |
| 9,677,118 B2 | 6/2017 | Zimmermann et al. |
| 10,081,839 B2 | 9/2018 | Rabinowitz et al. |
| 10,083,273 B2 | 9/2018 | Rabinowitz et al. |
| 2001/0051341 A1* | 12/2001 | Lo ................. C12Q 1/6879 435/6.12 |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0119004 A1 | 6/2003 | Wenz et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-brechot |
| 2005/0079535 A1* | 4/2005 | Kirchgesser ....... C12N 15/1003 435/6.12 |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0051799 A1* | 3/2006 | Iwaki ................. C12N 15/1006 435/6.12 |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216738 A1 | 9/2006 | Wada et al. |
| 2006/0281105 A1 | 12/2006 | Li et al. |
| 2007/0020640 A1 | 1/2007 | McCloskey et al. |
| 2007/0027636 A1 | 2/2007 | Rabinowitz |
| 2007/0042384 A1 | 2/2007 | Li et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |

(56) References Cited

U.S. PATENT DOCUMENTS

| | | |
|---|---|---|
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2012/0295819 A1 | 11/2012 | Leamon et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0162269 A1 | 6/2014 | Rabinowitz |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1* | 9/2014 | Srinivasan ............ C12Q 1/6806 506/2 |
| 2014/0287934 A1 | 9/2014 | Szelinger et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0147815 A1 | 5/2015 | Babiarz et al. |
| 2015/0197786 A1 | 7/2015 | Osborne et al. |
| 2015/0232938 A1 | 8/2015 | Mhatre |
| 2015/0265995 A1 | 9/2015 | Head et al. |
| 2016/0186253 A1 | 6/2016 | Talasaz et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2017/0121716 A1 | 5/2017 | Rodi et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0201995 A1 | 7/2018 | Rabinowitz et al. |
| 2018/0298439 A1 | 10/2018 | Ryan et al. |
| 2018/0300448 A1 | 10/2018 | Rabinowitz et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0256894 A1 | 8/2019 | Zimmermann et al. |
| 2019/0256908 A1 | 8/2019 | Rabinowitz et al. |
| 2019/0256912 A1 | 8/2019 | Rabinowitz et al. |
| 2019/0256919 A1 | 8/2019 | Babiarz et al. |
| 2019/0256931 A1 | 8/2019 | Babiarz et al. |
| 2020/0126634 A1 | 4/2020 | Sigurjonsson et al. |

FOREIGN PATENT DOCUMENTS

| | | |
|---|---|---|
| EP | 0270017 A2 | 6/1988 |
| EP | 1524321 A1 | 4/2005 |
| EP | 1524321 B1 | 7/2009 |
| EP | 2163622 A1 | 3/2010 |
| EP | 2128169 A1 | 12/2010 |
| EP | 2902500 A1 | 8/2015 |
| GB | 2488358 | 8/2012 |
| RU | 2290078 C1 | 12/2006 |
| WO | 200190419 A2 | 11/2001 |
| WO | 2002004672 A2 | 1/2002 |
| WO | 2002055985 A2 | 7/2002 |
| WO | 2003031646 A1 | 4/2003 |
| WO | 2003062441 A1 | 7/2003 |
| WO | 0190419 A9 | 11/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | 2007070482 A2 | 6/2007 |
| WO | 2007/117256 A1 | 10/2007 |
| WO | 2007132167 A2 | 11/2007 |
| WO | 2007/147076 A2 | 12/2007 |
| WO | 2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008059578 A1 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/036525 A2 | 3/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |
| WO | 2009146335 A1 | 12/2009 |
| WO | 2010017214 A1 | 2/2010 |
| WO | 2010/033652 A1 | 3/2010 |
| WO | 2010075459 | 7/2010 |
| WO | 2011041485 A1 | 4/2011 |
| WO | 2011057094 | 5/2011 |
| WO | 2011/090556 A1 | 7/2011 |
| WO | 2011087760 | 7/2011 |
| WO | 2011146632 A1 | 11/2011 |
| WO | 201283250 | 6/2012 |
| WO | 2012088456 A2 | 6/2012 |
| WO | 20120071621 | 6/2012 |
| WO | 2012108920 A1 | 8/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013052557 A2 | 4/2013 |
| WO | 2013/078470 A2 | 5/2013 |
| WO | 2013/086464 A1 | 6/2013 |

(56) References Cited

FOREIGN PATENT DOCUMENTS

| WO | 20130130848 | | 9/2013 |
|---|---|---|---|
| WO | 2013/181651 | A1 | 12/2013 |
| WO | 2014/004726 | A1 | 1/2014 |
| WO | 2014/014497 | A1 | 1/2014 |
| WO | 20140018080 | | 1/2014 |
| WO | 2014/035986 | A1 | 3/2014 |
| WO | 2014/122288 | A1 | 8/2014 |
| WO | 2014/149134 | A2 | 9/2014 |
| WO | 2014/151117 | A1 | 9/2014 |
| WO | 2015/100427 | A1 | 7/2015 |
| WO | 2015/164432 | A1 | 10/2015 |
| WO | 2016/009059 | A1 | 1/2016 |
| WO | 2016/065295 | A1 | 4/2016 |
| WO | 2016/138080 | A1 | 9/2016 |
| WO | 2016/193490 | A1 | 12/2016 |
| WO | 2017/058784 | A1 | 4/2017 |
| WO | 2018/083467 | A1 | 5/2018 |
| WO | 2018/106798 | A1 | 6/2018 |
| WO | 2018/156418 | A1 | 8/2018 |
| WO | 2020/131699 | A2 | 6/2020 |

OTHER PUBLICATIONS

Illumina, "Patent Owner Illumina's Preliminary Response to Petition", Oct. 17, 2018, 75 pgs.
Illumina, "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.
Illumina, "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.
Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.
Lu, I. et al., "Establishment of a system based on universal multiplex-PCR for screening genetically modified crops", Anal. Bioanal. Chem, vol. 396, Oct. 24, 2009, 2055-2064.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Minkoff, E. et al., "Stem Cells, Cell Division, and Cancer", Biology Today Third Edition, Chapter 12, 2004, 10 pages.
Natera, Inc., , "Corporate Disclosure Statement", May 16, 2019, 2 pages.
Natera, Inc., , "Declaration of Sandra L. Haberny", May 16, 2019, 3 pages.
Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., , "Exhibit 8 EHRICH Invalidity Chart", Aug. 20, 2018, 16 pages.
Natera, Inc., , "Exhibits A-H to Haberny Declaration", May 16, 2019, 192 pages.
Natera, Inc., , "Motion to Dismiss", May 16, 2019, 2 pages.
Natera, Inc., , "Opening Brief in Support of Motion to Dismiss", May 16, 2019, 26 pages.
Natera, Inc., , "Petitioner Reply Per Board Order of Nov. 2, 2018 (Paper No. 10)", Nov. 9, 2018, 8 pgs.
Shen, R. et al., "High-throughput SNP genotyping on universal bead arrays", Mutation Research, vol. 573, Feb. 11, 2005, 70-82.
Wang, D. G. et al., "Large-Scale Identification, Mapping, and Genotyping of Single-Nucleotide Polymorphisms in the Human Genome", Science, vol. 280, May 15, 1998, 1077-1082.
Wang, T.L. et al., "Digital karyotyping", PNAS, vol. 99, No. 25, Dec. 10, 2002, 16156-16161.
Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.
Anker, P. et al., "Detection of circulating tumour DNA in the blood (plasma/serum) of cancer patients", Cancer and Metastasis Reviews, vol. 18, 1999, 65-73.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Chan, K.C. et al., "Size Distributions of Maternal and Fetal DNA in Maternal Plasma", Clinical Chemistry, vol. 50, No. 1, 2004, 88-92.
Chen, X. Q. et al., "Microsatallite alterations in plasma DNA of small cell lung cancer patients", Nature Medicine, vol. 2, No. 9, Sep. 1996, 1033-1035.
Dodge, Y., "Bayes' Theorem", The Concise Encyclopedia of Statistics, 2008, 30-31.
Geiss, G. K. et al., "Direct multiplexed measurement of gene expression with color-coded probe pairs", Nature Biotechnology, vol. 26, No. 3, Feb. 17, 2008, 317-325.
Gunderson, K. L. et al., "A genome-wide scalable SNP genotyping assay using microarray technology", Nature Genetics, vol. 37, No. 5, May 2005, 549-554.
Jenkins, S. et al., "High-throughput SNP genotyping", Comparative and Functional Genomics, vol. 3, Dec. 5, 2001, 57-66.
Kwok, P. Y., "High-throughput genotyping assay approaches", Pharmacogenomics, vol. 1, No. 1, 2000, 1-5.
Lander, E. S. et al., "Initial sequencing and analysis of the human genome", Nature, vol. 409, Feb. 15, 2001, 860-921.
Levsky, J. M. et al., "Fluorescence in situ hybridization: past, present and future", Journal of Cell Science, vol. 116, No. 14, 2003, 2833-2838.
Palomaki, G. E. et al., "DNA sequencing of maternal plasma to detect Down syndrome: An international clinical validation study", Genetics in Medicine, vol. 13, No. 1, Nov. 2011, 913-920.
Quinn, G. P. et al., "Experimental Design and Data Analysis for Biologists", Graphical Exploration of Data, 2002, 64-67.
Tebbutt, S. J. et al., "Microarray genotyping resource to determine population stratification in genetic association studies of complex disease", BioTechniques, vol. 37, Dec. 2004, 977-985.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
"Blast of AAAAAAAAATTTAAAAAAAAATTT(http://blast.ncbi.nlm.nih.gov/Blast.cgi, downloaded May 4, 2015)".
"CompetitivePCR Guide,", TaKaRa Biomedicals, Lit. # L0126 Rev. 8/99, 9 pgs.
"db Snp r52056688 (http://www.ncbi.nlm.nih.gov/projects/SNP/snp_ref.cgi?rs=2056688, downloaded May 4, 2015".
"Declaration by Dr. Zimmerman of Oct. 30, 2014 filed in 14/044434".
"European Application No. 014198110, European Search Report dated Apr. 28, 2015, 3 pages."
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.
"Merriam-Webster.com (http://www.merriam-webster.com/dictionary/universal, downloaded Jul. 23, 2014)".

(56) References Cited

OTHER PUBLICATIONS

"PRIMER3, information sheet, Sourceforge.net. [retrieved on Nov. 12, 2012]. Retrieved from the Internet: <URL:http://primer3.sourceforge.net/>", 2009, 1 pg.

PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).

Wikipedia (attached, available at https://en.wikipedia.org/wiki/Stimulant, accessed Mar. 14, 2016).

"How Many Carbs in a Potato?, [Online]", Retrieved from the Internet: <http://www.newhealthguide.org/How-Many-Carbs-In-A-Potato.html>, Nov. 1, 2014, 3 pages.

"Random variable", In the Penguin Dictionary of Mathematics. Retrieved from http://www.credoreference.com/entry/penguinmath/random_variable, 2008, 1 page.

Abbosh, C. et al., "Phylogenetic ctDNA analysis depicts early-stage lung cancer evolution", Nature, vol. 545, May 25, 2017, 446-451.

Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.

Agarwal, Ashwin. et al., "Commercial Landscape of Noninvasive Prenatal Testing in the United States", Prenatal Diagnosis,33, 2013, 521-531.

Alkan, Can et al., "Personalized Copy Number and Segmental Duplication Maps Using Next-Generation Sequencing", Nature Genetics, 41, 10, 2009, 1061-1068.

Allaire, F R., "Mate selection by selection index theory", Theoretical Applied Genetics, 57(6), 1980, 267-272.

Allawi, Hatim T. et al., "Thermodynamics of internal C•T Mismatches in DNA", Nucleic Acids Research, 26 (11), 1998, 2694-2701.

Aoki, Yasuhiro, "Statistical and Probabilistic Bases of Forensic DNA Testing", The Journal of the Iwate Medical Association, 2002, vol. 54, p. 81-94.

Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.

Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.

Bada, Michael A. et al., "Computational Modeling of Structural Experimental Data", Methods in Enzymology,317, 2000, 470-491.

Beaumont, Mark A et al., "The Bayesian Revolution in Genetics", Nature Reviews Genetics, 5, 2004, 251-261.

Beer, Alan E. et al., "The Biological Basis of Passage of Fetal Cellular Material into the Maternal Circulation", Annals New York Academy of Sciences, 731, 1994, 21-35.

Beerenwinkel, et al., "Methods for Optimizing Antiviral Combination Therapies", Bioinformatics, 19(1), 2003, i16-i25.

Beerenwinkel, N. et al., "Geno2pheno: estimating phenotypic drug resistance from HIV-1 genotypes", Nucleic Acids Research, 31(13), 2003, 3850-3855.

Benn, P. et al., "Non-Invasive Prenatal Testing for Aneuploidy: Current Status and Future Prospects", Ultrasound Obstet Gynecol, 42, 2013, 15-33.

Benn, P et al., "Non-Invasive prenatal Diagnosis for Down Syndrome: the Paradigm Will Shift, but Slowly", Ultrasound Obstet. Gynecol., 39, 2012, 127-130.

Bentley, David R et al., "Accurate Whole Human Genome Sequencing Using Reversible Terminator Chemistry", Nature, 456, 6, 2008, 53-59.

Bermudez, M. et al., "Single-cell sequencing and mini-sequencing for preimplantation genetic diagnosis", Prenatal Diagnosis, 23, 2003, 669-677.

Bevinetto, Gina, Bevinetto (5 Foods All Pregnant Women Need, American Baby, available at http://www.parents.com/pregnancy/mybody/nutrition/5greatpregnancyfoods/, Apr. 15, 2008).

Bianchi, D W. et al., "Fetal gender and aneuploidy detection using fetal cells maternal blood: analysis of NIFTY I data", Prenat Diagn 2002; 22, 2002, 609-615.

Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.

Bisignano, et al., "PGD and Aneuploidy Screening for 24 Chromosomes: Advantages and Disadvantages of Competing Platforms", Reproductive BioMedicine Online, 23, 2011, 677-685.

Bodenreider, O., "The Unified Medical Language System (UMLS): Integrating Biomedical Terminology", Nucleic Acids Research, 32, (Database issue), 2004, D267-D270.

Breithaupt, Holger, "The Future of Medicine", EMBO Reports, 21(61), 2001, 465-467.

Brownie, Jannine et al., "The Elimination of Primer-Dimer Accumulation in PCR", Nucleic Acids Research, 25(16), 1997, 3235-3241.

Butler, J. et al., "The Development of Reduced Size STR Amplicons as Tools for Analysis of Degraded DNA*", Journal of Forensic Sciences, vol. 48, No. 5, 2003, 1054-1064.

Cairns, Paul et al., "Homozygous Deletions of 9p21 in Primary Human Bladder Tumors Detected by Comparative Multiplex Polymerase Chain Reaction", Cancer Research, 54, 1994, 1422-1424.

Caliendo, Angela, "Multiplex PCR and Emerging Technologies for the Detection of Respiratory Pathogens", Clinical Infectious Diseases, 52(4), 2011, S326-S330.

Cansar,, "Hs-578-T—Copy Number Variation—Cell Line Synopsis", ICR Cancer Research UK, Retrieved on Mar. 26, 2018 from https://cansar.icr.ac.uk/cansar/cell-lines/Hs-578- T/copy_number_variation/chromosome_8/, Mar. 26, 2018, 50 pgs.

Carnevale, Alessandra et al., "Attitudes of Mexican Geneticists Towards Prenatal Diagnosis and Selective Abortion", American Journal of Medical Genetics, 75, 1998, 426-431.

Carvalho, B. et al., "Exploration, normalization, and genotype calls of high-density oligonucleotide SNP array data", Biostatistics, vol. 8, No. 2, 2007, 485-499.

Casbon, J. A. et al., "A method for counting PCR template molecules with application to next-generation sequencing", Nucleic Acids Research, vol. 39, No. 12, Apr. 13, 2011, 1-8.

Chakraborty, R. et al., "Paternity Exclusion by DNA Markers: Effects of Paternal Mutations", Journal of Forensic Sciences, vol. 41, No. 4, Jul. 1996, 671-677.

Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.

Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.

Chetty, Shilpa et al., "Uptake of Noninvasive Prenatal Testing (NIPT) in Women Following Positive Aneuploidy Screening", Prenatal Diagnosis,33, 2013, 542-546.

Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.

Chiu, Rossa W. et al., "Effects of Blood-Processing Protocols on Fetal and Total DNA Quantification in Maternal Plasma", Clinical Chemistry, 47(9), 2001, 1607-1613.

Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.

Chiu, Rossa W.K. et al., "Non-Invasive Prenatal Diagnosis by Single Molecule Counting Technologies", Trends in Genetics, 25 (7), 2009, 324-331.

Chiu, Rossa W.K. et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.

Choi, M. et al., "Genetic diagnosis by whole exome capture and massively parallel DNA sequencing", PNAS, vol. 106, No. 45, Nov. 10, 2009, 19096-19101.

(56) References Cited

OTHER PUBLICATIONS

Chu, T. et al., "Statistical Considerations for Digital Approaches to Non-Invasive Fetal Genotyping", Bioinformatics (Advance Access publication), 26 (22), 2010, 2863-2866.

Chu, Tianjiao et al., "Statistical Model for Whole Genome Sequencing and its Application to Minimally Invasive Diagnosis of Fetal Genetic Disease", Bioinformatics, 25(10), 2009, 1244-1250.

Chu, Tianjiao. et al., "A Novel Approach Toward the Challenge of Accurately Quantifying Fetal DNA in Maternal Plasma", Prenatal Diagnosis,30, 2010, 1226-1229.

Cole, Neal W. et al., "Hyperglycemia-Induced Membrane Lipid Peroxidation and Elevated Homocysteine Levels are Poorly Attenuated by Exogenous Folate in Embryonic Chick Brains", Comparative Biochemistry and Physiology, Part B, 150, 2008, 338-343.

Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.

Cossu, Gianfranco et al., "Rh D/d Genotyping by Quantitative Polymerase Chain Reaction and Capillary Zone Electrophoresis", Electrophoresis, 17, 1996, 1911-1915.

Coyle, J. F. et al., "Standards for detailed clinical models as the basis for medical data exchange and decision support", International Journal of Medical Informatics, 69(2-3), 2003, 157-174.

Craig, D. W. et al., "Identification of genetic variants using barcoded multiplexed sequencing", Nature Methods, vol. 5, Oct. 2008, 887-893.

Cross, Jillian et al., "Resolution of trisomic mosaicism in prenatal diagnosis: estimated performance of a 50K SNP microarray", Prenat Diagn 2007; 27, 2007, 1197-1204.

D'Aquila, Richard et al., "Maximizing sensitivity and specificity of PCR by pre-amplification heating", Nucleic Acids Research, 19(13), 1991, p. 3749.

Daruwala, Raoul-Sam et al., "A Versatile Statistical Analysis Algorithm to Detect Genome Copy Number Variation", PNAS, 101(46), 2004, 16292-16297.

De Bruin, E. et al., "Spatial and temporal diversity in genomic instability processes defines lung cancer evolution", Science, vol. 346, No. 6206, Oct. 10, 2014, 251-256.

De Vries, et al., "Diagnostic genome profiling in mental retardation", Am J Hum Genet, 77, published online Aug. 30, 2005, 2005, 606-616.

Deangelis, M. et al., "Solid-phase Reversible Immobilization for the Isolation of PCR Products", Nucleic Acids Research, 23 (22), 1995, 4742-4743.

Devaney, S. et al., "Noninvasive Fetal Sex Determination Using Cell-Free Fetal DNA: A Systematic Review and Meta-analysis", JAMA, 306 (6), 2011, 627-636.

Dhallan, et al., "Methods to Increase the Percentage of Free Fetal DNA Recovered from the Maternal Circulation", JAMA, 291(9), 2004, 1114-1119.

Dhallan, Ravinder et al., "A non-invasive test for prenatal diagnosis based on fetal DNA present in maternal blood: a preliminary study", The Lancet, 369, 2007, 474-481.

Dieffenbach, C W. et al., "General concepts for PCR primer design", Genome Research. PCR methods and Applications vol. 3, 1993, S30-S37.

Ding, C et al., "Direct molecular haplotyping of long-range genomic DNA with M1-PCR", PNAS 100(13), 2003, 7449-7453.

Dohm, J. et al., "Substantial Biases in Ultra-Short Read Data Sets From High-Throughput DNA Sequencing", Nucleic Acids Research, 36 (16), e105, 2008, 10 pgs.

Dolganov, Gregory et al., "A Novel Method of Gene Transcript Profiling in Airway Biopsy Homogenates Reveals Increased Expression of a Na -K+ -Ci-Cotransporter (NKCC1) in Asthmatic Subjects", Genome Res.,11, 2001, 1473-1483.

Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.

Donoso, P. et al., "Current Value of Preimplantation Genetic Aneuploidy Screening in IVF", Human Reproduction Update, 13(1), 2007, 15-25.

Echeverri, et al., "Caffeine's Vascular Mechanisms of Action", International Journal of Vascular Medicine vol. 2010(2010), 10 pages, Aug. 25, 2010.

Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.

Eichler, H , "Mild Course of Fetal Rh D Haemolytic Disease due to Maternal Alloimmunisation to Paternal HLA Class I and II Antigens", Vox Sang, 68, 1995, 243-247.

Ellison, Aaron M. , "Bayesian Inference in Ecology", Ecology Letters, vol. 7, 2004, 509-520.

Ellonen, P. et al., "Development of SNP Microarray for Supplementary Paternity Testing", International Congress Series, 1261, 2004, 12-14.

EP06838311.6, "European Communication and Extended European Search Report", dated Dec. 30, 2008, 8 pgs.

EP08742125.1, "European Communication pursuant to Article 94(3) EPC and Examination Report", dated Feb. 12, 2010, 5 pgs.

Fan, et al., "Whole-genome molecular haplotyping of single cells", Nature Biotechnology, vol. 29, No. 1, Jan. 1, 2011, 51-57.

Fan, Christina H. et al., "Non-Invasive Prenatal Measurement of the Fetal Genome", Nature, doi:10.1038/nature11251, 2012, 26 pgs.

Fan, Christina H et al., "Noninvasive Diagnosis of Fetal Aneuploidy by Shotgun Sequencing DNA from Maternal Blood", PNAS, 105, 42, 2008, 16266-16271.

Fan, H. C. et al., "Microfluidic digital PCR enables rapid prenatal diagnosis of fetal aneuploidy", American Journal of Obstetrics & Gynecology, vol. 200, May 2009, 543.e1-543.e7.

Fan, H. Christina et al., "Sensitivity of Noninvasive Prenatal Detection of Fetal Aneuploidy from Maternal Plasma Using Shotgun Sequencing is Limited Only by Counting Statistics", PLoS ONE, vol. 5, Issue 5 (e10439), May 3, 2010, 1-6.

Fan, Jian-Bing et al., "Highly Parallel Genomic Assay", Nature Reviews, 7, 2006, 632-644.

Fazio, Gennaro. et al., "Identification of RAPD Markers Linked to Fusarium Crown and Root Rot Resistance (Frl) in Tomato", Euphytica 105, 1999, 205-210.

Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.

Fiorentino, F et al., "Strategies and Clinical Outcome of 250 Cycles of Preimplantation Genetic Diagnosis for Single Gene Disorders", Human Reproduction, 21, 3, 2006, 670-684.

Fiorentino, Francesco et al., "Short Tandem Repeats Haplotyping of the HLA Region in Preimplantation HLA Matching", European Journal of Human Genetics, 13, 2005, 953-958.

Ford, E. et al., "A method for generating highly multiplexed ChIP-seq libraries", BMC Research Notes, vol. 7, No. 312, May 22, 2014, 1-5.

Forejt, et al., "Segmental trisomy of mouse chromosome 17: introducing an alternative model of Down's syndrome", Genomics, 4(6), 2003, 647-652.

Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.

Fredriksson, et al., "Multiplex amplification of all coding sequences within 10 cancer genes by Gene-Collector", Nucleic Acids Research, 2007, vol. 35, No. 7 e47, 1-6.

Freeman, Jennifer L. et al., "Copy Number Variation: New Insights in Genome Diversity", Genome Research, 16, 2006, 949-961.

Frost, Mackenzie S et al., "Differential Effects of Chronic Pulsatile Versus Chronic Constant Maternal Hyperglycemia on Fetal Pancreatic B-Cells", Journal of Pregnancy, 2012 Article ID 812094, 2012, 8.

(56) References Cited

OTHER PUBLICATIONS

Fu, G. K. et al., "Counting individual DNA molecules by the stochastic attachment of diverse labels", PNAS, vol. 108, No. 22, May 31, 2011, 9026-9031.

Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.

Ganshirt-Ahlert, D. et al., "Ratio of Fetal to Maternal DNA is Less Than 1 in 5000 at different Gestational Ages in Maternal Blood", Clinical Genetics,38, 1990, 38-43.

Ganshirt-Ahlert, D. et al., "Fetal DNA in Uterine Vein Blood", Obstetrics & Gynecology, 80 (4), 1992, 601-603.

Ganshirt-Ahlert, Dorothee et al., "Three Cases of 45,X/46,XYnf Mosaicism", Human Genetics, 76, 1987, 153-156.

Garcia-Murillas, I. et al., "Mutation tracking in circulating tumor DNA predicts relapse in early breast cancer", Science Translational Medicine, vol. 7, No. 302, Aug. 26, 2015, 1-2.

Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.

Ghanta, Sujana et al., "Non-Invasive Prenatal Detection of Trisomy 21 Using Tandem Single Nucleotide Polymorphisms", PLoS ONE, 5 (10), 2010, 10 pgs.

Gjertson, David W. et al., "Assessing Probability of Paternity and the Product Rule in DNA Systems", Genetica, 96, 1995, 89-98.

Greenwalt, T. et al., "The Quantification of Fetomaternal Hemorrhage by an Enzyme-Linked Antibody Test with Glutaraldehyde Fixation", Vox Sang, 63, 1992, 268-271.

Guerra, J. , "Terminal Contributions for Duplex Oligonucleotide Thermodynamic Properties in the Context of Nearest Neighbor Models", Biopolymers, 95(3), (2010), 2011, 194-201.

Guetta, Esther et al., "Analysis of Fetal Blood Cells in the Maternal Circulation: Challenges, Ongoing Efforts, and Potential Solutions", Stem Cells and Development, 13, 2004, 93-99.

Guichoux, et al., "Current Trends in Microsatellite Genotyping", Molecular Ecology Resources, 11, 2011, 591-911.

Hall, M. , "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].

Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.

Hara, Eiji et al., "Subtractive cDNA cloning using oligo(dT)3o-latex and PCR: isolation of cDNA clones specific to undifferentiated human embryonal carcinoma cells", Nucleic Acids Research, 19(25), 1991, 7097-7104.

Hardenbol, P. , "Multiplexed Genotyping With Sequence-Tagged Molecular Inversion Probes", Nature Biotechnology, 21 (6), 2003, 673-678.

Hardenbol, Paul et al., "Highly multiplexed molecular inversion probe genotyping: Over 10,000 targeted SNPs genotyped in a singled tube assay", Genome Research, 15, 2005, 269-275.

Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.

Harper, J. C. et al., "Recent Advances and Future Developments in PGD", Prenatal Diagnosis, 19, 1999, 1193-1199.

Harton, G.L. et al., "Preimplantation Genetic Testing for Marfan Syndrome", Molecular Human Reproduction, 2 (9), 1996, 713-715.

Hawkins, T. et al., "Whole genome amplification—applications and advances", Current Opinion in Biotechnology, 13, 2002, 65-67.

Hayden, et al., "Multiplex-Ready PCR: A new method for multiplexed SSR and SNP genotyping", BMC Genomics 2008, 9(80), 1-12.

Hellani, A. et al., "Clinical Application of Multiple Displacement Amplification in Preimplantation Genetic Diagnosis", Reproductive BioMedicine Online, 10 (3), 2005, 376-380.

Hellani, Ali et al., "Multiple displacement amplification on single cell and possible PGD applications", Molecular Human Reproduction, 10(11), 2004, 847-852.

Hojsgaard, S. et al., "BIFROST—Block recursive models induced from relevant knowledge, observations, and statistical techniques", Computational Statistics & Data Analysis, 19(2), 1995, 155-175.

Hollas, B. et al., "A stochastic approach to count RN A molecules using DNA sequencing methods", Lecture Notes in Computer Science, vol. 2812, 2003, 55-62.

Holleley, et al., "Multiplex Manager 1.0: a Cross-Platform Computer Program that Plans and Optimizes Multiplex PCR", BioTechniques46:511-517 (Jun. 2009), 511-517.

Hollox, E. et al., "Extensive Normal Copy Number Variation of a β-Defensin Antimicrobial-Gene Cluster", Am. J. Hum. Genet., 73, 2003, 591-600.

Homer, et al., "Resolving Individuals Contributing Trace Amounts of DNA to Highly Complex Mixtures Using High-Density SNP Genotyping Microarrays", PLOS Genetics, 4(8), 2008, 9 pgs.

Hoogendoorn, Bastiaan et al., "Genotyping Single Nucleotide Polymorphisms by Primer Extension and High Performance Liquid Chromatography", Hum Genet, 104, 1999, 89-93.

Hospital, F. et al., "A General Algorithm to Compute Multilocus Genotype Frequencies Under Various Mating Systems" vol. 12, No. 6, Jan. 1. 1996 (Jan. 1, 1996), pp. 455-462.

Howie, et al., "Fast and accurate genotype imputation in genome-wide association studies through pre-phasing", Nature Genetics, vol. 44, No. 8, Jul. 22, 2012, 955-959.

Hu, Dong Gui et al., "Aneuploidy Detection in Single Cells Using DNA Array-Based Comparative Genomic Hybridization", Molecular Human Reproduction, 10(4), 2004, 283-289.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.

Illumina Catalog, "Paired-End Sample Preparation Guide, Illumina Catalog# PE-930-1 001, Part# 1005063 Rev. E", 2011, 1-40.

Ishii, et al., "Optimization of Annealing Temperature to Reduce Bias Caused by a Primer Mismatch in Multitemplate PCR", Applied and Environmental Microbiology, Aug. 2001, p. 3753-3755.

Jabara, C. B. et al., "Accurate sampling and deep sequencing of the HIV-1 protease gene using a Primer ID", PNAS, vol. 108, No. 50, Dec. 13, 2011, 20166-20171.

Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.

Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.

Jamal-Hanjani, M. et al., "Tracking Genomic Cancer Evolution for Precision Medicine: The Lung TRACERx Study", PLOS Biology, vol. 12, No. 7, Jul. 2014, 1-7.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T. , "Next generation sequencing technologies", Drug Discovery Today: Technologies, vol. 2, No. 3, 2005, 255-260.

Johnson, D.S. et al., "Comprehensive Analysis of Karyotypic Mosaicism Between Trophectoderm and Inner Cell Mass", Molecular Human Reproduction, 16(12), 2010, 944-949.

(56) References Cited

OTHER PUBLICATIONS

Johnson D.S, et al., "Preclinical Validation of a Microarray Method for Full Molecular Karyotyping of Blastomeres in a 24-h Protocol", Human Reproduction, 25 (4), 2010, 1066-1075.

Kaplinski, Lauris et al., "MultiPLX: Automatic Grouping and Evaluation of PCR Primers", Bioinformatics, 21(8), 2005, 1701-1702.

Kazakov, V.I. et al., "Extracellular DNA in the Blood of Pregnant Women", Tsitologia, vol. 37, No. 3, 1995, 1-8.

Kijak, G. et al., "Discrepant Results in the Interpretation of HIV-1 Drug-Resistance Genotypic Data Among Widely Used Algorithms", HIV Medicine, 4, 2003, 72-78.

Kim, H. et al., "Whole-genome and multisector exome sequencing of primary and post-treatment glioblastoma reveals patterns of tumor evolution", Genome Research, vol. 25, No. 3, Feb. 3, 2015, 316-327.

Kinde, I. et al., "Detection and quantification of rare mutations with massively parallel sequencing", PNAS, vol. 108, No. 23, Jun. 7, 2011, 9530-9535.

Kinnings, S. L. et al., "Factors affecting levels of circulating cell-free fetal DNA in maternal plasma and their implications for noninvasive prenatal testing", Prenatal Diagnosis, vol. 35, 2015, 816-822.

Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.

Kivioja, T. et al., "Counting absolute numbers of molecules using unique molecular identifiers", Nature Methods, Advance Online Publication, Nov. 20, 2011, 1-5.

Konfortov, Bernard A. et al., "An Efficient Method for Multi-Locus Molecular Haplotyping", Nucleic Acids Research, 35(1), e6, 2007, 8 pgs.

Krjutskov, K. et al., "Development of a single tube 640-plex genotyping method for detection of nucleic acid variations on microarrays", Nucleic Acids Research, vol. 36, No. 12, May 23, 2008, 7 pages.

Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.

Lambert-Messerlian, G. et al., "Adjustment of Serum Markers in First Trimester Screening", Journal of Medical Screening, 16 (2), 2009, 102-103.

Lathi, Ruth B. et al., "Informatics Enhanced SNP Microarray Analysis of 30 Miscarriage Samples Compared to Routine Cytogenetics", PLoS ONE, 7(3), 2012, 5 pgs.

Leary, R. J. et al., "Development of Personalized Tumor Biomarkers Using Massively Parallel Sequencing", Science Translational Medicine, vol. 2, No. 20, Feb. 24, 2010, 1-8.

Leary, Rebecca J et al., "Detection of Chromosomal Alterations in the Circulation of Cancer Patients with Whole-Genome Sequencing", Science Translational Medicine, 4, 162, 2012, 12.

Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.

Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.

Li, Ying et al., "Size Separation of Circulatory DNA in Maternal Plasma Permits Ready Detection of Fetal DNA Polymorphisms", Clinical Chemistry, 50, 6, 2004, 1002-1011.

Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.

Liao, J. et al., "An Alternative Linker-Mediated Polymerase Chain Reaction Method Using a Dideoxynucleotide to Reduce Amplification Background", Analytical Biochemistry 253, 137-139 (1997).

Liew, Michael et al., "Genotyping of Single-Nucleotide Polymorphisms", Clinical Chemistry, 50(7), 2004, 1156-1164.

Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.

Lo, et al., "Digital PCR for the Molecular Detection of Fetal Chromosomal Aneuploidy", PNAS, vol. 104, No. 32, Aug. 7, 2007, 13116-13121.

Lo, et al., "Fetal Nucleic Acids in Maternal Blood: the Promises", Clin. Chem. Lab. Med., 50(6), 2012, 995-998.

Lo, et al., "Free Fetal DNA in Maternal Circulation", JAMA, 292(23), (Letters to the Editor), 2004, 2835-2836.

Lo, , "Non-Invasive Prenatal Diagnosis by Massively parallel Sequencing of Maternal Plasma DNA", Open Biol 2: 120086, 2012, 1-5.

Lo, et al., "Prenatal Sex Determination by DNA Amplification from Maternal Peripheral Blood", The Lancet,2, 8676, 1989, 1363-1365.

Lo, et al., "Rapid Clearance of Fetal DNA from Maternal Plasma", Am. J. Hum. Genet., 64, 1999, 218-224.

Lo, et al., "Strategies for the Detection of Autosomal Fetal DNA Sequence from Maternal Peripheral Blood", Annals New York Academy of Sciences,731, 1994, 204-213.

Lo, et al., "Two-way cell traffic between mother and fetus: biologic and clinical implications", Blood, 88(11), Dec. 1, 1996, 4390-4395.

Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.

Lo, Y.M. Dennis et al., "Maternal Plasma DNA Sequencing Reveals the Genome-Wide Genetic and Mutational Profile of the Fetus", Science Translational Medicine 2 (61), 2010, 13.

Lo, Y.M. Dennis et al., "Plasma placental Rna allelic ratio permits noninvasive prenatal chromosomal aneuploidy detection", Nature Medicine, 13 (2), 2007, 218-223.

Lo, Y.M. Dennis et al., "Presence of Fetal DNA in Maternal Plasma and Serum", The Lancet, 350, 1997, 485-487.

Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.

Lo, Y-M.D et al., "Detection of Single-Copy Fetal DNA Sequence from Maternal Blood", The Lancet, 335, 1990, 1463-1464.

Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.

Lo, Y-M.D. et al., "Detection of Fetal RhD Sequence from Peripheral Blood of Sensitized RhD-Negative Pregnant Women", British Journal of Haematology, 87, 1994, 658-660.

Lo, Y-M.D. et al., "Prenatal Determination of Fetal RhD Status by Analysis of Peripheral Blood of Rhesus Negative Mothers", The Lancet, 341, 1993, 1147-1148.

Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

Ma, Xiaotu et al., "Rise and fall of subclones from diagnosis to relapse in pediatric B-acute lymphoblastic leukaemia", Nature Communications, vol. 6, Mar. 19, 2015, 1-12.

Maniatis, T. et al., "In: Molecular Cloning: A Laboratory Manual", Cold Spring Harbor Laboratory, New York, Thirteenth Printing, 1986, 458-459.

Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.

Margulies, M. et al., "Genome sequencing in microfabricated high-density picolitre reactors", Nature, vol. 437, Sep. 15, 2005, 376-380.

(56) References Cited

OTHER PUBLICATIONS

Margulies, M. et al., "Genome sequencing in microfabricated high-density picolitre reactors plus Supplemental Methods", Nature, vol. 437, Sep. 15, 2005, 40 pgs.
Markoulatos, P. et al., "Multiplex Polymerase Chain Reaction: A Practical Approach", Journal of Clinical Laboratory Analysis, vol. 16, 2002, 47-51.
May, Robert M. , "How Many Species Are There on Earth?", Science, 241, Sep. 16, 1988, 1441-1449.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
McCloskey, M. L. et al., "Encoding PCR Products with Batch-stamps and Barcodes", Biochem Genet., vol. 45, Oct. 23, 2007, 761-767.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
Mennuti, M. et al., "Is It Time to Sound an Alarm About False-Positive Cell-Free DNA Testing for Fetal Aneuploidy?", American Journal of Obstetrics, 2013, 5 pgs.
Merriam-Webster, , "Medical Definition of Stimulant", http://www.merriam-webster.com/medical/stimulant, Mar. 14, 2016, 7 pages.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Miner, B. E. et al., "Molecular barcodes detect redundancy and contamination in hairpin-bisulfite PCR", Nucleic Acids Research, vol. 32, No. 17, Sep. 30, 2004, 1-4.
Morand, et al., "Hesperidin contributes to the vascular protective effects of orange juice: a randomized crossover study in healthy volunteers", Am J Clin Nutr. Jan. 2011;93(1 ):73-80. Epub Nov. 10, 2010.
Munne, S. et al., "Chromosome abnormalities in human embryos", Human Reproduction update, 4 (6), 842-855.
Munne, S. et al., "Chromosome Abnormalities in Human Embryos", Textbook of Assisted Reproductive Techniques, 2004, pp. 355-377.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V. , "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
O'Malley, R. et al., "An adapter ligation-mediated PCR method for high-throughput mapping of T-DNA inserts in the *Arabidopsis* genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of Φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Papageorgiou, Elisavet A. et al., "Fetal-Specific DNA Methylation Ratio Permits Noninvasive Prenatal Diagnosis of Trisomy 21", Nature Medicine (advance online publication),17, 2011, 5 pgs.
Pathak, A. et al., "Circulating Cell-Free DNA in Plasma/Serum of Lung Cancer Patients as a Potential Screening and Prognostic Tool", Clinical Chemistry, 52, 2006, 1833-1842.
PCT/US2006/045281, "International Preliminary Report on Patentability", dated May 27, 2008, 1 pg.
PCT/US2006/045281, "International Search Report and Written Opinion", dated Sep. 28, 2007, 7 pgs.
PCT/US2008/003547, "International Search Report", dated Apr. 15, 2009, 5 pgs.
PCT/US2009/034506, "International Search Report", dated Jul. 8, 2009, 2 pgs.
PCT/US2009/045335, "International Search Report", dated Jul. 27, 2009, 1 pg.
PCT/US2009/052730, "International Search Report", dated Sep. 28, 2009, 1 pg.
PCT/US2010/050824, "International Search Report", dated Nov. 15, 2010, 2 pgs.
PCT/US2011/037018, , "International Search Report", dated Sep. 27, 2011, 2 pgs.
PCT/US2011/061506, "International Search Report", dated Mar. 16, 2012, 1 pgs.
PCT/US2011/066938, "International Search Report", dated Jun. 20, 2012, 1 pg.
PCT/US2012066339, "International Search Report", dated Mar. 5, 2013, 1 pg.
PCT/US2013/028378, "International Search Report and Written Opinion", dated May 28, 2013, 11 pgs.
PCT/US2013/57924, "International Search Report and Written Opinion", dated Feb. 18, 2014, 8 pgs.
PCT/US2014/051926, "International Search Report and Written Opinion", dated Dec. 9, 2014, 3 pgs.

(56) References Cited

OTHER PUBLICATIONS

Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends in Genetics, 10, 6, 1994, 204-209.
Pergament, E. et al., "Single-Nucleotide Polymorphism-Based Noninvasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M., "Overcoming the Challenges of Multiplex PCR", Biocompare Editorial Article, NULL, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Relative Expression Software Tool (REST©) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics,1(5), 2008, 1-15.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterility, vol. 97, No. 2, Feb. 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Ragoussis, J., "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.

Rechitsky, Svetlana et al., "Preimplantation Genetic Diagnosis with HLA Matching", Reproductive Bio Medicine Online, 9, 2, 2004, 210-221.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet:<http://www.youandyourfamily.com/article.php?story=Eating+by+Trimester>, 2014, 3.
Riley, D. E., "DNA Testing: An Introduction for Non-Scientists An Illustrated Explanation", Scientific Testimony: An Online Journal, http://www.scientific.org/tutorials/articles/riley/riley.html, Apr. 6, 2005, 22 pages.
Rogaeva, E. et al., "The Solved and Unsolved Mysteries of the Genetics of Early-Onset Alzheimer's Disease", NeuroMolecular Medicine, vol. 2, 2002, 1-10.
Roper, Stephen M. et al., "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L. M., "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Sahota, A., "Evaluation of Seven PCR-Based Assays for the Analysis of Microchimerism", Clinical Biochemistry, vol. 31, No. 8., 1998, 641-645.
Samango Sprouse, C. et al., "SNP-based non-invasive prenatal testing detects sex chromosome aneuploidies with high accuracy", Prenatal Diagnosis, vol. 33, 2013, 643-649.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, vol. 46, No. 1, 2001, 43-46.
Schmitt, M. W. et al., "Detection of ultra-rare mutations by next-generation sequencing", PNAS, vol. 109, No. 36, Sep. 4, 2012, 14508-14513.
Schoumans, J et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1. 2002 (Jan. 1, 2002), pp. 227-228.
Shaw-Smith, et al., "Microarray Based Comparative Genomic Hybridisation (array-CGH) Detects Submicroscopic Chromosomal

(56) References Cited

OTHER PUBLICATIONS

Deletions and Duplications in Patients with Learning Disability/ Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, Zhiyong, "MPprimer: a program for reliable multiplex PCR primer design", BMC Bioinformatics 2010, 11:143, 1-7.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balancing Primer Efficiencies and Improving Detection Success", Methods in Ecology and Evolution, 3, 2012, 898-905.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spiro, Alexander et al., "A Bead-Based Method for Multiplexed Identification and Quantitation of DNA Sequences Using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Steyerberg, E.W et al., "Application of Shrinkage Techniques in Logistic Regression Analysis: A Case Study", Statistica Neerlandica, 55(1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., "Inferring combined CNV/SNP haplotypes from genotype data", Bioinformatics, vol. 26, No. 11,1, Jun. 1, 2010, 1437-1445.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory, 2003. Proceedings, 2003, 286.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Ten Bosch, J. , "Keeping Up With the Next Generation Massively Parallel Sequencing in Clinical Diagnostics", Journal of Molecular Diagnostics, vol. 10, No. 6, 2008, 484-492.
Tewhey, R. et al., "The importance of phase information for human genomics", Nature Reviews Genetics, vol. 12, No. 3, Mar. 1, 2011, 215-223.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Turner, E. et al., "Massively Parallel Exon Capture and Library-Free Resequencing Across 16 Genomes", Nature Methods, 6 (5), 2009, 315-316.
Vallone, Peter , "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.

(56) References Cited

OTHER PUBLICATIONS

Wapner, R. et al., "First-Trimester Screening for Trisomies 21 and 18", The New England Journal of Medicine, vol. 349, No. 15, Oct. 9, 2003, 1405-1413.

Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.

Wells, D , "Microarray for Analysis and Diagnosis of Human Embryos", 12th International Congress on Prenatal Diagnosis and Therapy, Budapest, Hungary, 2004, 9-17.

Wells, Dagan , "Advances in Preimplantation Genetic Diagnosis", European Journal of Obstetrics and Gynecology and Reproductive Biology, 115S, 2004, S97-S101.

Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.

Wen, Daxing et al., "Universal Multiples PCR: A Novel Method of Simultaneous Amplification of Multiple DNA Fragments", Plant Methods, 8(32), NULL, 2012, 1-9.

Wikipedia, "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.

Wilton, et al., "Birth of a Healthy Infant After Preimplantation Confirmation of Euploidy by Comparative Genomic Hybridization", N. Engl. J. Med., 345(21), 2001, 1537-1541.

Wilton, L. , "Preimplantation Genetic Diagnosis and Chromosome Analysis of Blastomeres Using Comparative Genomic Hybridization", Human Reproduction Update, 11 (1), 2005, 33-41.

Wright, C. et al., "The use of cell-free fetal nucleic acids in maternal blood for non-invasive prenatal diagnosis", Human Reproduction Update, vol. 15, No. 1, 2009, 139-151.

Wright, C. F. et al., "Cell-free fetal DNA and RNA in maternal blood: implications for safer antenatal testing", BMJ, vol. 39, Jul. 18, 2009, 161-165.

Wu, Y. Y. et al., "Rapid and/or high-throughput genotyping for human red blood cell, platelet and leukocyte antigens, and forensic applications", Clinica Chimica Acta, vol. 363, 2006, 165-176.

Xia, Tianbing et al., "Thermodynamic Parameters for an Expanded Nearest-Neighbor Model for Formation of RNA Duplexes with Watson-Crick Base Pairs", Biochemistry, 37, 1998, 1471 9-14735.

Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.

Xu, S. et al., "Circulating tumor DNA identified by targeted sequencing in advanced-stage non-small cell lung cancer patients", Cancer Letters, vol. 370, 2016, 324-331.

Yeh, Iwei et al., "Knowledge Acquisition, Consistency Checking and Concurrency Control for Gene Ontology (GO)", Bioinformatics, 19, 2, 2003, 241-248.

You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.

Zhang, Rui et al., "Quantifying RNA allelic ratios by microfluidic multiplex PCR and sequencing", Nature Methods, 11(1), 2014, 51-56.

Zhao, Xiaojun. et al., "An Integrated View of Copy Number and Allelic Alterations in the Cancer Genome Using Single Nucleotide Polymorphism Arrays", Cancer Research,64, 2004, 3060-3071.

Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.

Zhou, W. et al., "Counting Alleles Reveals a Connection Between Chromosome 18q Loss and Vascular Invasion", Nature Biotechnology, 19, 2001, 78-81.

Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.

* cited by examiner

COMPOSITIONS, METHODS, AND KITS FOR ISOLATING NUCLEIC ACIDS

CROSS REFERENCE TO RELATED APPLICATIONS

This application claims priority to U.S. Provisional Application No. 62/461,735 filed Feb. 21, 2017, which is incorporated herein by reference in its entirety.

BACKGROUND

Non-invasive and minimally invasive liquid biopsy tests utilize sample material collected from external secretions or by needle aspiration for analysis. The extracellular nuclear DNA present in the cell-free fraction of bodily fluids such as urine, saliva and other glandular secretions, cerebrospinal and peritoneal fluid, and plasma or serum from blood, contain sufficient amounts of target sequences to support accurate detection of genetic anomalies that underlie many disorders that could otherwise be difficult or impossible to diagnosis outside of expensive medical biopsy procedures bearing substantial risk. In blood, the circulating cell free DNA (cfDNA) fraction represents a sampling of nucleic acid sequences shed into the blood from numerous sources which are deposited there as part of the normal physiological condition. The origin of a majority of cfDNA can be traced to either hematological processes or steady-state turnover of other tissues such as skin, muscle, and major organ systems. Of great clinical importance, was the discovery that a significant and detectable fraction of cfDNA derives from exchange of fetal DNA crossing the placental boundary, and from immune-mediated, apoptotic, or necrotic cell lysis of tumor cells, or cells infected by viruses, bacterium, or intracellular parasites. This makes plasma an extremely attractive specimen for molecular analytical tests and, in particular, test that leverage the power of deep sequencing for diagnosis and detection. However, a need exists for methods capable of reliably extracting cfDNA from a biological sample such as plasma.

SUMMARY

The present inventions are directed to compositions, methods, and kits for binding and/or isolating nucleic acids from a biological sample. In a first aspect, the inventions described herein relate to a composition for isolating nucleic acids from a biological sample, comprising a chaotropic compound and a solvent, wherein the solvent comprises a nitrile compound, or tetrahydrofuran (THF), or a combination thereof.

In a second aspect, the inventions described herein relate to a method for binding nucleic acids to a matrix, comprising contacting the nucleic acids from a biological sample with the matrix in the presence of a chaotropic compound and a solvent, wherein the solvent comprises a nitrile compound, or tetrahydrofuran (THF), or a combination thereof, thereby binding the nucleic acids to the matrix.

In a third aspect, the inventions described herein relate to a kit for isolating nucleic acids from a biological sample, comprising a binding buffer, wherein the binding buffer comprises a chaotropic compound and a solvent, wherein the solvent comprises a nitrile compound, or tetrahydrofuran (THF), or a combination thereof. The binding buffer can be mixed with a biological sample that has been pre-treated with a digestion buffer comprising a protease in order to facilitate binding of nucleic acids to a matrix.

These and other features, together with the organization and manner of operation thereof, will become apparent from the following detailed description when taken in conjunction with the accompanying drawings. The description that follows illuminates several surprising and unexpected findings. First, that aprotic solvents such as acetonitrile, other nitrile compounds and THF, whose physical properties differ in many respects from protic solvents typically employed in nucleic acid extraction methods, remained sufficiently miscible in aqueous high concentration chaotropic compounds and promoted highly efficient binding of nucleic acids from biological samples to a purification matrix such as, for example, fibrous bosilicate glass (FIGS. 2-7). Second, the combination of acetonitrile and a chaotropic compound returned a consistent and reproducible increase in computed fetal fraction estimates by an NGS based NIPT analysis (FIG. 9). Third, the use of acetonitrile to establish the nucleic acid binding state significantly reduced the time required to filter lysates through a binding matrix (FIG. 10), and furthermore, the reduction in contact time did not reduce the efficiency of nucleic acid binding to the matrix, as might have been expected.

DETAILED DESCRIPTION

Figure 1:
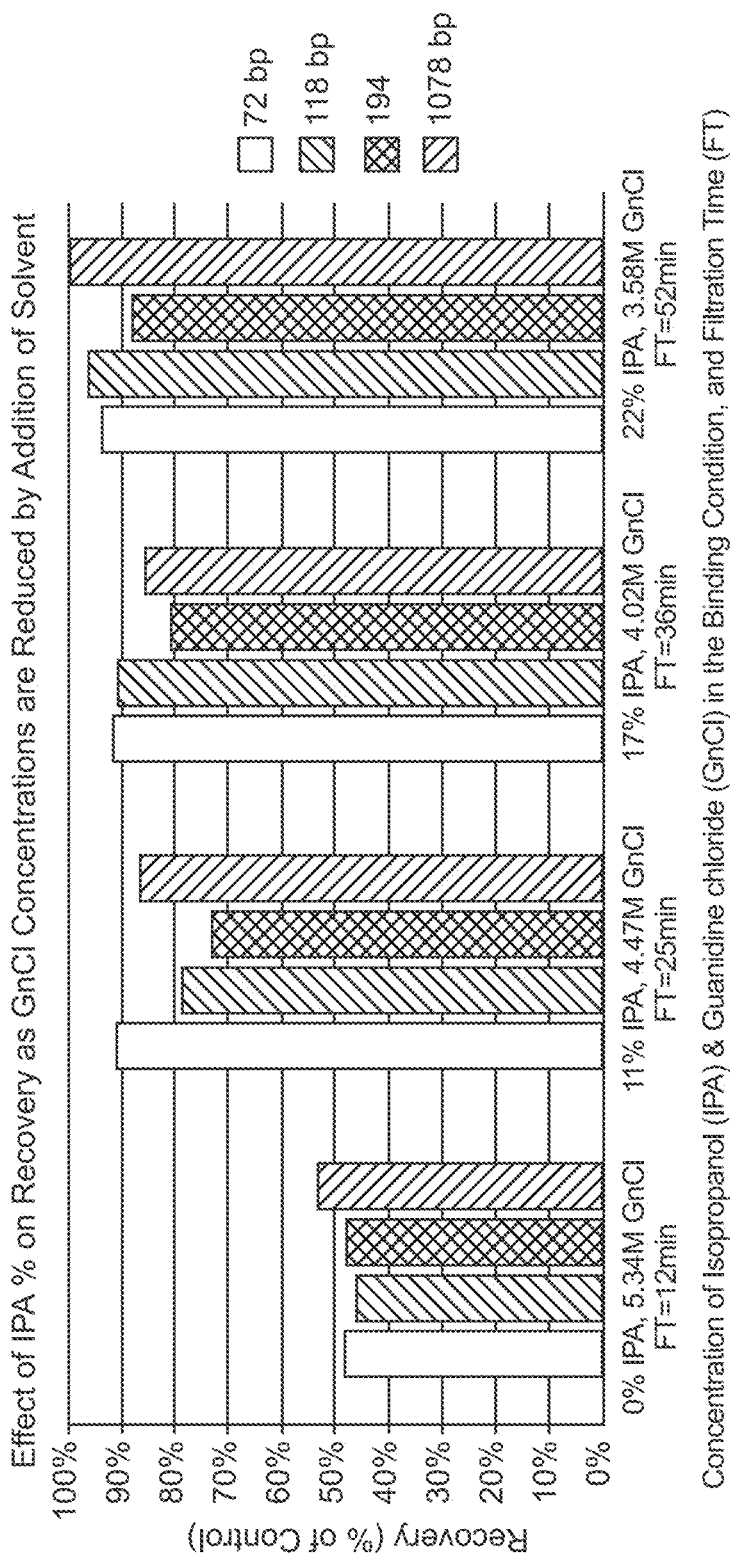
FIG. 1 shows recovery of DNA as a function of the concentration of isopropanol (IPA) and guanidine chloride (GnCl) in the nucleic acid binding state. Recovery of short dsDNA increased as the IPA concentration was raised and GnCl concentrations fell as a certain amount of volume was displaced by the added solvent. Exogenous DNA targets were spiked after plasma proteolysis and quantified by real time PCR and standard curve methods. Percent recovery of target fragments was determined by comparing against spike controls assembled by adding the original spike amount to eluates recovered from matched plasma samples by DNA isolation methods similar to the test method. Each test sample was normalized with buffer to account for the volume of spike targets added to recovery controls.

Reference will now be made in detail to some specific embodiments of the invention contemplated by the inventors for carrying out the invention. Certain examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details.

Various techniques and mechanisms of the present invention will sometimes be described in singular form for clarity. However, it should be noted that some embodiments include multiple iterations of a technique or multiple instantiations of a mechanism unless noted otherwise.

Introduction

Characteristics of cfDNA in the Circulation.

The half-life of cfDNA can be longer than naked DNA spiked into fresh, unpreserved, plasma or when injected into the bloodstream in vivo. This can be due to the fact that circulating nuclear DNA remains in tight association with core and linker histones which protect two wraps or gyres of DNA, in mononucleosomes and chromatosomes, from active nucleases in blood or plasma, thus preserving fragments of ~130 to ~170 base pairs (bp) in length. Fragments of two or three times this length can also be recovered from plasma, demonstrating that oligonucleosomes and oligochromatosomes can exist in the circulation as well. In addition to chromatinized DNA, both DNA and various RNA species survive for a substantial length of time in the circulation within membrane bound microvesicles (exosomes), actively shed by cells via exocytosis and blebbing. The steady-state concentration of circulating cell free DNA (cfDNA) fluctuates in the ng/mL range, and reflects the net balance between release of fragmented chromatin into the bloodstream and the rate of clearance by nucleases, hepatic uptake and cell mediated engulfment. Normal and health compromised individuals, exhibit cfDNA concentrations averaging 1 and 40 ng/mL of plasma (*J. Clin. Inv.* (1975) 56:512). No single source or mechanism can explain from where or how such short chromatin bits enter the circulation with such regularity, but as discussion, the process is dominated by erythrocytic apoptosis in the blood and bone marrow. Lesser contributions from apoptotic, necrotic and traumatic cell death, coupled with macrophage destruction throughout the body (*Cancer. Res.* (2001) 61:1659) spill cfDNA sequences into the blood that potentially include rare variants indicative of latent disease or serious fetal genetic anomalies. When coupled to the power of next generation genetic testing, cfDNA can provide unprecedented access to genetic information from disease states that might elude conventional detection, or where the site of origin is inaccessible to biopsy. Accurate and early detection of tumor associated genetic mutation, rearrangements, copy number variation, insertions/deletions or fusions is possible through deep analysis of cfDNA from plasma.

Preservation of cfDNA for Genetic Analysis.

The key to liquid biopsy approaches which target cfDNA, is the ability to bind and purify sufficient quantities of the highly fragmented DNA from blood plasma collected by needle stick, typically from an arm vein. With respect to non-invasive prenatal testing and cancer detection, a huge problem is presented by the fact that an overwhelming majority of cfDNA in blood comes from normal cells. This background of normal DNA dilutes the far scarcer fragments originating from the developing fetus or tumor cells. Thus care needs to be taken to preserve circulating nucleosomes from the time of blood collection to sample processing, and to prevent or minimize further dilution of cfDNA by genomic DNA released by lysis of nucleated cells. Such precautions begin at blood collection with the utilization of blood collection tubes (BCT's) which contain anticlotting and cell stabilizing agents which prevent lysis of mononuclear cells during storage for up to 14 days. To compensate for the low endogenous levels of cfDNA in plasma and to improve the odds of sampling a comparatively rare population of sequences of interest, tests routinely call for the processing of large volumes, up to 10 mL, of plasma through DNA extraction methods. This necessitates collection of at least two 10 mL blood samples to generate one 10 mL plasma sample. The present invention describes methods for release of bound cfDNA from nucleoprotein complexes contained in human plasma and the high efficiency capture and recovery (>85-95%) of the liberated cfDNA fragments from 10 mL of plasma. The method is extendable to isolation of cfDNA from serum and other body fluids.

DNA Extraction from Large Volume Plasma Samples.

The isolation and purification of cfDNA from plasma poses a particular set of challenges due to the low starting concentration, matrix complexities, and the variable nature of plasma samples collected by venipuncture into vacuum tubes. Conventionally, 10 to 60 ng of cfDNA is recoverable from 10 mL of human plasma, and the average small size of DNA fragments make them difficult to capture and retain on solid supports through sequential wash steps. Plasma is a complicated fluid, and in comparison to the total mass of other macromolecular constituents (e.g., proteins, lipids and protein-lipid complexes), cfDNA represents a tiny fraction. Any successful plasma nucleic acid extraction process needs to accomplish three things to isolate cfDNA in pure form and at high rates of recovery. First, the protein complexes that serve to protect cfDNA (i.e., chromatinized DNA in the form of mono-, di-, tri-nucleosomes or longer) from nucleases need to be deconstructed to release cfDNA and expose it for capture on solid phases. Second, the macromolecular components which predominate in plasma (e.g., albumin, immunoglobulins, fibrinogen/fibrin, free hemoglobin, proteinase inhibitors, nucleases, lipids and lipoprotein complexes) need to be dissolved, degraded, solubilized, or neutralized to prevent them from interacting with released cfDNA or the capture matrix in ways that would interfere with (for example clog or foul) or reduce the efficiency of nucleic acid binding. Third, the establishment of a chemical environment, binding proficient condition or nucleic acid binding state that supports and promotes complete, preferential, stable, and reversible interaction of nucleic acids, in particular cfDNA fragments of all sizes, with the solid phase support material or capture matrix comprised of glass fiber or silica.

Release of cfDNA by Proteolysis, Chemical Denaturation or Both.

The two main methods used to disrupt stable noncovalent DNA-protein interactions are chemical denaturation and enzymatic destruction. Early methods employed organic liquid phase extraction utilizing phenol and phenol-chloroform mixtures to disintegrate nucleoprotein complexes and sequester proteins and lipids into the organic phase while partitioning the highly hydrophilic DNA and RNA into the aqueous phase in very pure form. Phenol-chloroform methods proved highly efficient and delivered DNA highly suitable for enzymatic manipulation. However, user and environmental safety, ease of use considerations, and practical difficulties of scaling large volume extractions to phenol-chloroform methods have led to its replacement with safer, highly scalable solid phase methods that can more easily purify nucleic acids from almost any starting material. One of the earliest solid phase methods used to purify DNA was described by E. M. Southern (*J. Mol. Biol.* (1975) 94:51-70) where the DNA excised from agarose hydrogels was recovered following dissolution in strongly chaotropic salts, sodium perchlorate or sodium iodide (NaI), followed direct DNA capture on hydroxyapatite (mineralized calcium phosphate) particles, washed and eluted into a low ionic strength buffer. Vogelstein and Gillespie (*PNAS, USA* (1979)76:615-619) later improved upon this earliest example by substituting powdered glass for hydroxyapatite and captured DNA from bits of agarose gels dissolved in saturated NaI. Excess NaI was removed by washing glass particles in 50% buffered ethanol and the bound DNA eluted in Tris buffered saline, EDTA. This method, which utilized glass or silica as a solid support to bind nucleic acids in the presence of high salt, followed by washes in high percentage alcohol to remove contaminants, and elution in low ionic strength buffers, forms the basis for most commercial nucleic acid purification kits on the market. These safer and highly scalable methods work by exploiting the strong yet reversible hydrophilic interaction promoted between DNA and silanols and siloxanes on the surface of glass and silica (*Colloids and Surfaces, A: Physiochemical and Engineering Aspects*, (2000)173:1-38) in high salt solutions. Unlike phenol-chloroform methods which efficiently denature and strip bound proteins off DNA and simultaneously denature, solvate and move proteins, lipids and other contaminants into the organic phase, solid phase extraction methods need to deal with DNA bound proteins and background sample contaminants differently. Proteolysis of protein-DNA complexes is the most widely employed method of releasing proteins bound to DNA and for degrading other protein contaminants contained in the starting sample. Still other effective methods utilize only strong chemical denaturants to disrupt protein tertiary and secondary structure, dissociate DNA/RNA from chromatin or binding proteins, and unfold other proteins contained in the sample to greatly diminish their interference with the glass/silica solid phase during DNA capture. Boom et al. (*J Clin Micro*. (1990) 28(3):495-503) were the first to detail the use of solid phase capture on powdered glass and diatomaceous silica from clinical samples such as serum and urine. Their method used a solid phase of glass or silica particles to adsorb nucleic acids from complex biological samples following direct chemical lysis in high concentrations of chaotropic salts.

Figure 8:
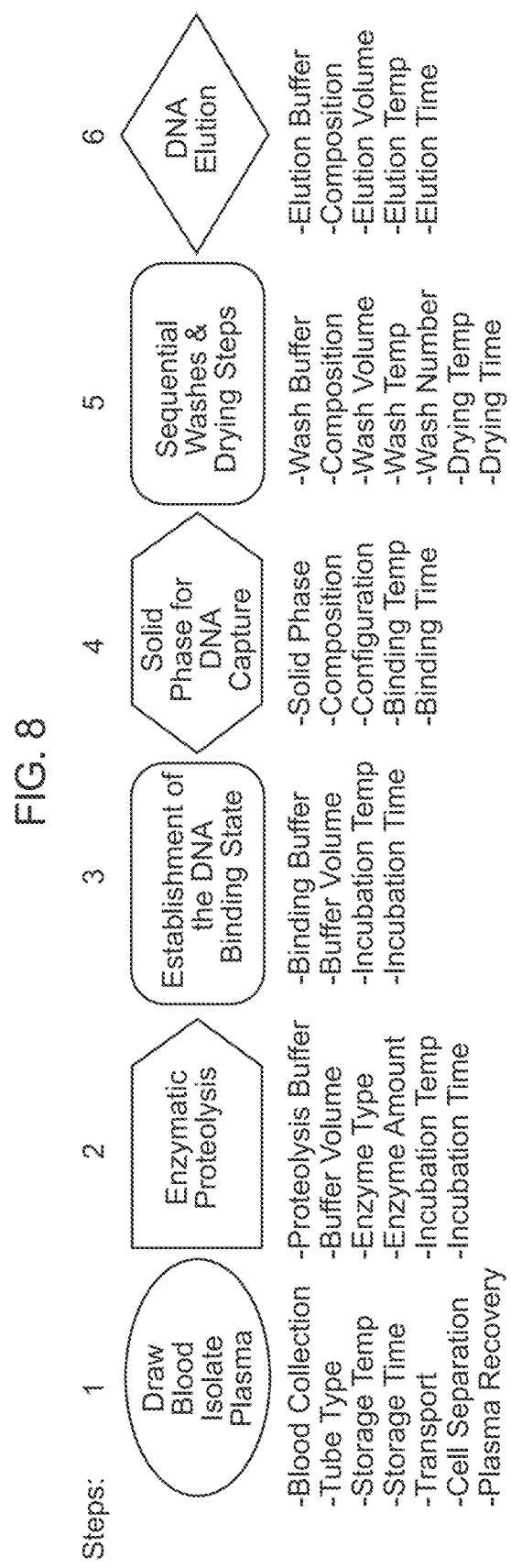
FIG. 8 shows a generalized Plasma ccfDNA Extraction Workflow.

A generalized scheme by which cfDNA can be isolated from plasma is presented in FIG. 8, which describes major effectors for each phase of the extraction. For cfDNA isolation by solid phase capture, plasma proteins and protein-DNA complexes are typically disrupted by a combination of proteolytic lysis and chemical lysis which sets up the nucleic acid binding state, a condition that necessitates the sequential, serial addition of two buffers, Proteolysis Buffer and Binding Buffer to samples, separated by an incubation step (see FIG. 8, steps 2 & 3). The constituents of Proteolysis Buffer and Binding Buffer should be optimized to effect complete proteolysis and the combination of which should establish a chemical environment that promotes highly efficient interaction of nucleic acids (DNA/RNA) with a Solid Phase or Binding Matrix (FIG. 8, step 4) such as glass fiber or silica particles. Proteinase K is the most common broad spectrum protease used for proteolytic lysis in DNA extraction methods. It is a stable serine protease that is active under a wide range of pH, temperature, salt, solvent, and detergent concentrations. The activity of Proteinase K peaks in the presence of moderate denaturants, 2-4 molar chaotropic salts and ionic detergents, which act both to stimulate enzymatic activity and increase substrate accessibility by destabilizing protein secondary structure. At completion, Proteinase K digestion will have reduced polypeptides to small di- and tri-peptides, and in the process degraded itself by autodigestion, thus eliminating the vast majority of enzyme added to samples. Proteolysis Buffer is a key additive in DNA extraction methods, and critical to DNA isolation from complex biological samples. In sample mixtures, Proteolysis Buffer is designed to preserve target nucleic acids, establish optimum conditions for proteolysis, solubilize lipids and microvesicles, breakdown colloids and particulate matter, and prevent precipitation over the course of protease reactions. Moreover, Proteolysis Buffer must be compatible with Binding Buffers which are added to samples following proteolysis in order to complete the denaturation process and establish the nucleic acid binding state (see FIG. 8, step 3). Binding Buffers act to chemically complete denaturation, quench remaining PK activity, and sets up a nucleic acid binding state that ensures high efficiency capture of short nucleic acids to silicate supports (see FIG. 8, steps 3 & 4). Available methods designed to isolate cfDNA from plasma or serum typically begin with a proteinase K lysis step initiated under moderately harsh conditions optimized for protease activity, followed by much harsher and highly denaturing chemical lysis steps optimized for DNA binding. Proteolysis Buffers and Binding Buffers serve two separate yet complimentary functions when combined with sample matrices in an ordered fashion, and form an articulated chemical system that supports high level solid phase adsorption of large and small nucleic acid fragments contained in complex biological samples.

The Importance of Small Fragment Recovery to NIPT Analysis by NGS

Figure 9:
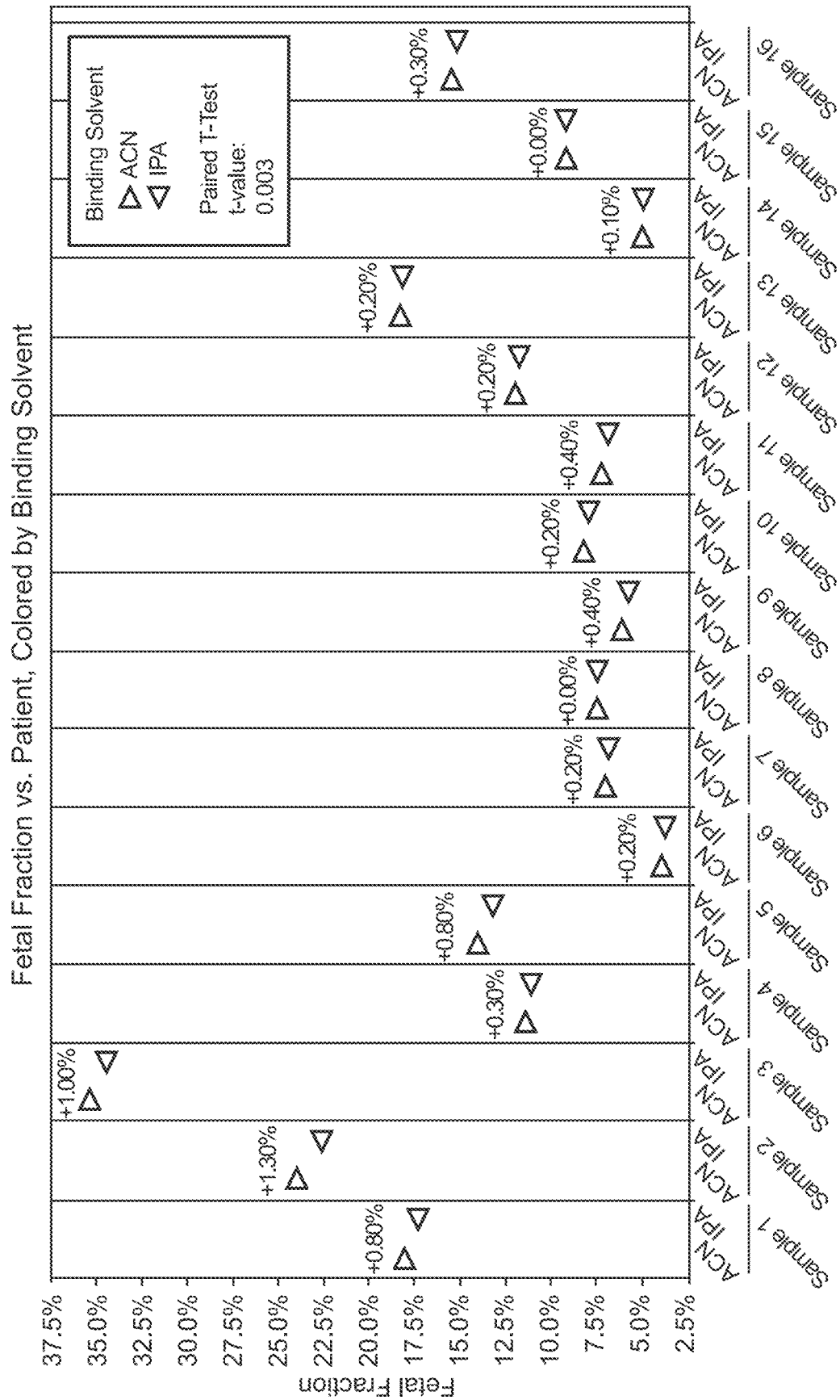
FIG. 9 details the increased recovery of fetal cfDNA by when ACN and GnCl are present in the nucleic acid binding state, as revealed by NIPT analysis. Fetal fraction estimates derived from the ratio of fetal to maternal SNPs are shown. The pairwise comparison included 16 maternal plasma samples isolated with two different optimized methods, one utilizing acetonitrile (ACN) and one isopropyl alcohol (IPA), to establish the nucleic acid binding state. Differences in fetal fraction ((ACN)-(IPA)) are shown above each matched pair. A paired t-test reveals a statistically significant increase (t=0.003) when acetonitrile was used to establish the nucleic acid binding state.

Many next generation genetic tests utilize plasma cfDNA from a simple blood draw as an input. This patient sampling technique known as a liquid biopsy is considered a non-invasive medical procedure valuable in cancer surveillance (*J Clin Oncol*. (2014) 32(6):579-586) and detection, and prenatal health screening (*Annu Rev Genomics Hum Genet*. (2012)13:285-306). Non-invasive prenatal tests (NIPT's) which utilize cfDNA from the plasma of pregnant women to detect chromosomal aneuploidies and microdeletions that may affect child health, are examples of such liquid biopsy based NGS tests. Most NGS assays begin with the preservation and amplification of the very small amounts of cfDNA obtained from plasma samples in a process known as library preparation. Construction of the library immortalizes the original cfDNA isolate and uniformly multiplies the sample through a series of molecular reactions that enzymatically repair, tail, and amplify fragments to prepare them for NGS analysis. In the NIPT assay referred to herein, libraries are subject to massively multiplexed amplification reactions that amplify single nucleotide polymorphisms (SNPs) used in the genetic analysis. The amplified SNP targets are then barcoded and readied for NGS sequencing. Sequence data is processed and allelic designations for each SNP are assigned to the mother or fetus (i.e., of paternal origin) according to a bimodal mixture model of homozygous (AA) or heterozygous (AB) allele distribution (*Bioinformatics*, 28(2):2883-2890). A higher fraction of fetal cfDNA in plasma isolates leads to a greater proportion of fetal SNP's out of the total (maternal+fetal) for each target SNP detected. A higher fetal fraction produces a greater divergence between the fetal genotype and the underlying maternal genotype, and thus increases the call confidence of ploidy estimates at the chromosome and locus level. More than one factor can profoundly influence the fetal fraction in cfDNA preparations, most critical is the storage condition and anticoagulant preservative used in blood collection tubes and the time between collection and plasma isolation. Conditions that minimize lysis of leucocytes significantly reduces leakage of maternal genomic DNA into the plasma, and thereby increase the fraction of fetal cfDNA as a percentage of total. Additionally, DNA purification methods that recover the broadest range of DNA sizes, particularly small fragments <100 bp in length, will ensure yield of the highest fetal fraction. This derives from the fact that circulating fetal DNA is on average ~23 bp shorter (143 bp vs 166 bp) than maternal cfDNA (*PNAS, USA* (2016) 113(50) E8159-E8168). Most recent evidence, based on the analysis of ssDNA libraries, suggests that much more cfDNA shorter in length is present (*Cell* (2016) 164:57-68), but indeed much of it may be excluded by the extraction method and library construction processes themselves (PNAS, USA (2016) 112(11):3178-3179). Thus plasma cfDNA extraction methods that rescue short <100 bp and very short <75 bp, and very very short <50 bp cfDNA fragments may well be expected to return higher fetal fraction estimates than methods that do not. FIG. 9 compares the fetal fraction estimates from 16 paired maternal samples where plasma cfDNA was isolated with IPA or ACN used as the co-solvent to establish the nucleic acid binding state. A highly statistically significant increase in the average fetal fraction was obtained from the otherwise identical analysis treatment of the cfDNA isolated with acetonitrile compared to isopropanol. This result is surprising and it was not anticipated that an increase in fetal fraction would result from the substitution of a protic solvent such as IPA with the aprotic solvent ACN. Though highly unexpected, the increase in fetal fraction could be explained by an improve preservation and subsequent recovery of short, very short and perhaps very very short cfDNA fragments.

Composition for Isolating Nucleic Acids

Many embodiments of the invention described herein relate to a composition for isolating nucleic acids from a biological sample, comprising a chaotropic compound and a solvent, wherein the solvent comprises an aprotic solvent such as a nitrile compound, tetrahydrofuran, or a combination thereof.

In some embodiments, the solvent comprises a nitrile compound. The nitrile compound can be, for example, acetonitrile (ACN), propionitrile (PCN), butyronitrile (BCN), isobutylnitrile (MCN), or a combination thereof.

In a particular embodiment, the nitrile compound is ACN. The composition can comprise, for example, about 10% to about 20% of ACN, or about 13% to about 18% of ACN, or about 15% of ACN.

In some embodiments, the composition comprises less than 10%, or less than 5%, or less than 2%, or less than 1% of alcohol, or substantially or totally free of alcohol. In some embodiments, the composition comprises less than 10%, or less than 5%, or less than 2%, or less than 1% of propanol such as isopropanol, or substantially or totally free of isopropanol. In some embodiments, the composition comprises less than 10%, or less than 5%, or less than 2%, or less than 1% of non-water protic solvents, or substantially or totally free of non-water protic solvents. The pH of the composition can be, for example, about 4 to about 10, or about 4 to about 5, or about 5 to about 6, or about 6 to about 7, or about 7 to about 8, or about 8 to about 9, or about 9 to about 10, or about 4 to about 8, or about 4.5 to about 6, or about 4.9 to about 5.1.

The chaotropic compound can be, for example, guanidine chloride (GnCl), urea, thiourea, guanidine thiocyanate, NaI, guanidine isothiocyanate, arginine, hydrogen perchlorate or perchlorate salt of Li+, Na+, K+, or a combination thereof.

In a particular embodiment, the chaotropic compound is GnCl. The composition can comprise, for example, about 3.5 M to about 6 M of GnCl, or about 4 M to about 5 M of GnCl, or about 4.4 M of GnCl.

In some embodiments, the composition further comprises a chelating compound. The chelating compound can be, for example, ethylenediaminetetraccetic (EDTA), ethyleneglycol-bis(2-aminoethylether)-N,N,N',N'-tetraacetic acid (EGTA), citric acid, N,N,N',N'-Tetrakis(2-pyridylmethyl) ethylenediamine (TPEN), 2,2'-Bipyridyl, deferoxamine methanesulfonate salt (DFOM), 2,3-Dihydroxybutanedioic acid (tartaric acid), or a combination thereof. In a particular embodiment, the chelating compound is EDTA.

In some embodiments, the composition further comprises a detergent. The detergent can be, for example, Triton X-100, Tween 20, N-lauroyl sarcosine, sodium dodecylsulfate (SDS), dodecyldimethylphosphine oxide, sorbitan monopalmitate, decylhexaglycol, 4-nonylphenyl-polyethylene glycol, or a combination thereof.

In a particular embodiment, the detergent is Triton X-100. The composition can comprise, for example, about 3% to about 6% of Triton X-100, or about 4% to about 5% of Triton X-100, or about 4.5% of Triton X-100.

In some embodiments, the composition further comprises nucleic acids. The nucleic acids can comprise, for example, DNAs and/or RNAs.

The nucleic acids can comprise, for example, maternal nucleic acids or fetal nucleic acids. The nucleic acids can comprise, for example, cell free nucleic acids or circuiting tumor nucleic acids. The cell free nucleic acids may be obtained from a sample of a maternal blood, plasma, or serum. The cell free nucleic acids can comprise, for example, cell free fetal DNA and cell free maternal DNA.

The nucleic acids can be, for example, about 50 to about 1200 base pairs in length, or about 70 to about 500 base pairs in length, or about 100 to about 200 base pairs in length, or about 130 to about 170 base pairs in length.

In some embodiments, the composition further comprises a matrix. The matrix can comprise, for example, siliceous materials, silica gel, glass, glass fiber, zeolite, aluminum oxide, titanium dioxide, zirconium dioxide, kaolin, gelatinous silica, magnetic particles, ceramics, polymeric supporting materials, or a combination thereof. In a particular embodiment, the matrix comprises glass fiber.

It was surprising and highly unexpected that such highly efficient recovery of nucleic acids, in particular cfDNA from plasma, could be achieved when protic solvents such as ethanol, propanol, or isopropanol were replaced by the aprotic solvents of the nitrile series including acetonitrile ((ACN), ethyl nitrile or methyl cyanide), propionitrile ((PCN), propyl nitrile or ethyl cyanide), butyronitrile ((BCN) butane nitrile or propyl cyanide), and isobutylnitrile ((IBCN), isobutyl nitrile or isopropyl cyanide), in the presence of a chaotropic compound through binding to a matrix such as glass fiber or silica. Just as unexpected was the fact that this combination also increased the calculated fetal fraction deriving from a SNP based NIPT method, given that contact times between the glass fiber matrix and the DNA binding state were much shorter than under binding conditions established with IPA as a solvent.

Methods for Binding and Isolating Nucleic Acids

Further embodiments of the invention described herein relate to a method for binding nucleic acids to a matrix and isolating the nucleic acids, comprising contacting the nucleic acids from a biological sample with a matrix in the presence of a chaotropic compound and a solvent, thereby binding the nucleic acids to the matrix, wherein the solvent comprises an aprotic solvent such as a nitrile compound, tetrahydrofuran, or a combination thereof.

In some embodiments, the nucleic acids are contacted with the matrix in the presence of a nitrile compound selected from ACN, PCN, BCN, IBCN, or a combination thereof. In a particular embodiment, the nitrile compound is ACN. The nucleic acids can be contacted with the matrix in the presence of, for example, about 10% to about 20% of ACN, or about 13% to about 18% of ACN, or about 15% of ACN.

In some embodiments, the nucleic acids are contacted with the matrix in the presence of less than 10% of alcohol, or less than 5% of alcohol, or less than 2% of alcohol, or less than 1% of alcohol, or substantially or totally in the absence of alcohol. In some embodiments, the nucleic acids are contacted with the matrix in the presence of less than 10% of propanol, or less than 5% of propanol, or less than 2% of propanol, or less than 1% of propanol such as isopropanol, or substantially or totally in the absence isopropanol. In some embodiments, the nucleic acids are contacted with the matrix in the presence of less than 10% of non-water protic solvents, or less than 5% of non-water protic solvents, or less than 2% of non-water protic solvents, or less than 1% of non-water protic solvents, or substantially or totally in the absence non-water protic solvents.

In some embodiments, the nucleic acids are contacted with the matrix in the presence of a chaotropic compound selected from GnCl, urea, thiourea, guanidine thiocyanate, NaI, guanidine isothiocyanate, D-/L-arginine, hydrogen perchlorate or perchlorate salt of Li+, Na+, K+, or a combination thereof. In a particular embodiment, the chaotropic compound is GnCl. The nucleic acids can be contacted with the matrix in the presence of, for example, about 3.5 M to about 6 M of GnCl, or about 4 M to about 5 M of GnCl, or about 4.4 M of GnCl.

In some embodiments, the nucleic acids are contacted with the matrix in the presence of a chelating compound selected from EDTA, EGTA, citric acid, TPEN, 2,2'-Bipyridyl, DFOM, tartaric acid, or a combination thereof. In a particular embodiment, the chelating compound is EDTA.

In some embodiments, the nucleic acids are contacted with the matrix in the presence of a detergent selected from Triton X-100, Tween 20, N-lauroyl sarcosine, SDS, dodecyldimethylphosphine oxide, sorbitan monopalmitate, decylhexaglycol, 4-nonylphenyl-polyethylene glycol, or a combination thereof. In a particular embodiment, the detergent is Triton X-100. The nucleic acids can be contacted with the matrix in the presence of, for example, about 3% to about 6% of Triton X-100, or about 4% to about 5% of Triton X-100, or about 4.5% of Triton X-100.

In some embodiments, the nucleic acids comprise maternal nucleic acids or fetal nucleic acids. In some embodiments, the nucleic acids are cell free nucleic acids or circuiting tumor nucleic acids. In some embodiments, the cell free nucleic acids are obtained from a sample of a maternal blood, plasma, or serum. In some embodiments, the cell free nucleic acids comprise, for example, cell free fetal DNA and cell free maternal DNA.

The nucleic acids can be, for example, about 50 to about 1200 base pairs in length, or about 70 to about 500 base pairs in length, or about 100 to about 200 base pairs in length, or about 130 to about 170 base pairs in length. In one embodiment, the nucleic acids comprise DNAs. In another embodiment, the nucleic acids comprise RNAs.

In some embodiments, the matrix comprises siliceous materials, silica gel, glass, glass fiber, zeolite, aluminum oxide, titanium dioxide, zirconium dioxide, kaolin, gelatinous silica, magnetic particles, ceramics, polymeric supporting materials, and or a combination thereof. In a particular embodiment, the matrix comprises glass fiber.

In some embodiments, the method further comprises incubating a biological sample comprising the nucleic acids with a protease such as proteinase K, prior to contacting the nucleic acids with the matrix. The biological sample can be, for example, a sample of a maternal blood, plasma, or serum.

In some embodiments, the method further comprises washing the matrix with at least one washing buffer to remove impurities. In some embodiments, the method further comprises drying the matrix. In some embodiments, the method further comprises eluting the nucleic acids from the matrix with an elution buffer.

In some embodiments, the contacting step binds at least 40%, at least 50%, or at least 60%, or at least 70%, or at least 80%, or at least 90%, of nucleic acids having a length of about 72 bp that are present in the composition to the matrix. In some embodiments, the contacting step binds at least 40%, at least 50%, or at least 60%, or at least 70%, or at least 80%, or at least 90%, of nucleic acids having a length of about 118 bp that are present in the composition to the matrix. In some embodiments, the contacting step binds at least 40%, at least 50%, or at least 60%, or at least 70%, or at least 80%, or at least 90%, of nucleic acids having a length of about 194 bp that are present in the composition to the matrix. In some embodiments, the contacting step binds at least 30%, at least 40%, or at least 50%, or at least 60%, of nucleic acids having a length of about 50 bp that are present in the composition to the matrix.

Kits for Isolating Nucleic Acids

Additional embodiments of the invention described herein relate to a kit for isolating nucleic acids from a biological sample, comprising a binding buffer, wherein the binding buffer comprises a chaotropic compound and a solvent, wherein the solvent comprises an aprotic solvent such as a nitrile compound, tetrahydrofuran, or a combination thereof.

In some embodiments, the binding buffer comprises a nitrile compound selected from ACN, PCN, BCN, MCN, or a combination thereof. In a particular embodiment, the binding buffer comprises ACN. The binding buffer can comprise, for example, about 15% to about 35% of ACN, or about 20% to about 30% of ACN, or about 25% of ACN.

In some embodiments, the binding buffer comprises less than 5% of alcohol, or less than 2% of alcohol, or less than 1% of alcohol, or less than 0.1% of alcohol, or comprises no alcohol. In some embodiments, the binding buffer comprises less than 5% of propanol, or less than 2% of propanol, or less than 1% of propanol, or less than 0.1% of propanol, or comprises no propanol such as isopropanol. In some embodiments, the binding buffer comprises less than 5% of non-water protic solvents, or less than 2% of non-water protic solvents, or less than 1% of non-water protic solvents, or less than 0.1% of non-water protic solvents, or comprises no non-water protic solvents. The pH of the binding buffer can be, for example, about 4 to about 10, or about 4 to about 5, or about 5 to about 6, or about 6 to about 7, or about 7 to about 8, or about 8 to about 9, or about 9 to about 10, or about 4 to about 8, or about 4.5 to about 6, or about 4.9 to about 5.1.

In some embodiments, the binding buffer comprises a chaotropic compound selected from GnCl, urea, thiourea, guanidine thiocyanate, NaI, guanidine isothiocyanate, D-/L-arginine, a perchlorate or perchlorate salt of Li+, Na+, K+, or a combination thereof. In a particular embodiment, the binding buffer comprises GnCl. The binding buffer can comprise, for example, about 5 M to about 8 M of GnCl, or about 5.6 M to about 7.2 M of GnCl, or about 6 M of GnCl.

In some embodiments, the binding buffer comprises a chelating compound selected from EDTA, EGTA, citric acid, TPEN, 2,2'-Bipyridyl, DFOM, tartaric acid, or a combination thereof. In a particular embodiment, the binding buffer comprises EDTA.

In some embodiments, the binding buffer comprises a detergent selected from Triton X-100, Tween 20, N-lauroyl sarcosine, SDS, dodecyldimethylphosphine oxide, sorbitan monopalmitate, decylhexaglycol, 4-nonylphenyl-polyethylene glycol, or a combination thereof. In a particular embodiment, the binding buffer comprises Triton X-100. The binding buffer can comprise, for example, about 1% to about 6% of Triton X-100, or about 2% to about 4% of Triton X-100, or about 3% of Triton X-100.

In some embodiments, the kit further comprises a digestion buffer comprising a protease such as proteinase K for digesting a biological sample. In some embodiments, the kit further comprises a washing buffer for washing the matrix to remove impurities. In some embodiments, the kit further comprises an elution buffer for eluting the nucleic acids from the matrix.

The binding buffer described herein can be used in a process for binding nucleic acids to a matrix, wherein the binding buffer is mixed with a biological sample (e.g., blood, plasma, or serum) that has been pre-treated with a digestion buffer comprising a protease such as proteinase K.

WORKING EXAMPLES

Example 1—Plasma Separation from Whole Blood

For each pair of blood collection tubes (BCT's) label one 15 mL conical tube and one 50 mL conical tube with the corresponding sample ID. Centrifuge BCTs at 2,000 rcf for 20 minutes at 22° C. to separate plasma from cells. Recover plasma from each BCT tube, without disturbing the pelleted cell layer, with a 10 mL serological pipette and transferred to a single 15 mL conical tube and remove remaining cell debris with a second 30 minute clarifying spin at 3,220 rcf at 22° C. Transfer the clarified plasma to 50 mL conical tubes avoiding pelleted material. Record volume and hemolysis grade for each plasma (i.e., yellow=None, pink/orange=Moderate, and red/dark red=Severe). Low volume (<6 mL) and severely hemolyzed plasma samples should not be processed. Begin the extraction process of plasma samples immediately or store frozen at −80° C.

Reagents:

| Formula | Reagent |
| --- | --- |
| Proteolysis Buffer | Triton X100 (Triton) |
| | Guanidine chloride (GnCl) |
| | Tris chloride (Tris-Cl) |
| | Ethlenediaminetetraacetic acid solution (EDTA) |
| Proteinase K Binding Buffer | Proteinase K from Tritirachium album |
| | Guanidine chloride (GnCl) |
| | Ethlenediaminetetraacetic acid solution (EDTA) |
| | Acetonitrile (ACN), Ethanenitrile, Ethyl nitrile, Cyanomethane, Methyl cyanide |
| | Triton X100 (Triton) |
| Wash Buffer 1 | Ethanol |
| | N-Lauroylsarcosine (NLS) |
| | Tris chloride (Tris-Cl) |
| | Ethlenediaminetetraacetic acid solution (EDTA) |
| | Distilled Water |
| Wash Buffer 2 | Ethanol |
| | Tris chloride Buffer Solution (Tris-Cl) |
| | Ethlenediaminetetraacetic acid solution (EDTA) |
| | Distilled Water |
| Elution Buffer | 10 mM Tris, 0.1 mM EDTA (pH 8) |

Example 2—Plasma Proteolysis/Establishing Proteinase K Digestion Conditions

Adjust the volume of fresh or thawed frozen plasma samples to 10 mL with 1×PBS and process immediately. Samples may be held at room temperature for up to 1 hour at room temperature or placed at 4° C. for wait times <12 hours. Prepare a 20 mg/mL Proteinase K solution less than 30 minutes prior to use. Reconstitute each 100 mg lyophilized vial of Proteinase K (PK) by adding 5 mL dH$_2$O followed by pipetting up and down at least 5× to completely wet the dried protein pellet. Close each PK vial and invert 10× to thoroughly dissolve the protease pellet and place on ice for at least 5 minutes to ensure complete dissolution. Gently flick or shake contents to the bottom of each vial and for consistency pool multiple vials to homogenize and place immediately on ice.

Initiate plasma proteolysis by adding 400 uL freshly prepared Proteinase K solution to each 10 mL plasma sample, cap and inverted each tube 5× to thoroughly mix. Place tubes back into racks at room temperature and proceed until PK has been added to all samples. Without delay, open caps and add 5 mL of PK Proteinase Buffer to each sample one at a time, quickly recap and mix by vortex at high speed for 5 seconds. Arrange samples in racks and submerge in a 42° C. water bath until the water level reaches at least three quarter height of the digestion mix and incubate for 45 minutes. Once the Proteinase K digestion process is complete, immediately move to the next step—Establishing the Nucleic Acid Binding State.

TABLE 1

Composition and Ranges for Enzymatic Plasma Proteolysis by Proteinase K

| Reagents | Range |
| --- | --- |
| Plasma (Sample) | 61.7-68.2% |
| Tris-Cl | 10-15 mM |
| EDTA | 2.5-10 mM |
| Guanidine chloride | 1.8-2.2M |
| Triton X100 | 5%-8% |
| Proteinase K | 0.4-0.6 mg/mL |

Example 3—Establishing the Nucleic Acid (NA) Binding State

Remove racks from the water and blot dry. If samples are to receive quantification targets, add the requisite amount of spike material to test samples, recap, and mix thoroughly. Uncap tubes and add Binding Buffer to each, recap, invert 10× to mix contents, and place back into the water bath at 42° C. for 10 minutes. This step completes the lysis process and sets up a chemical environment which favors binding of nucleic acids to solid phase glass fiber or silica supports. Remove the plasma lysates from the water bath, blot dry, and cool at room temperature (18-22° C.) for 10 minutes in preparation for Nucleic Acid Capture by Glass Fiber Vacuum Filtration

TABLE 3

Composition and Ranges for the Nucleic Acid Binding State

| Reagents | Range* |
|---|---|
| *Plasma (Sample)*** | *27.5-30.5%* |
| *Tris-Cl* | *1.5-2.2 mM* |
| *Proteinase K (Inactivated)* | — |
| Triton X100 | 4%-5% |
| EDTA | 3-5 mM |
| Guanidine chloride | 4.2-4.5M |
| Acetonitrile | 13-18% |

*Ranges listed are working ranges expected to give high level recovery of short cfDNA fragments.
**Reagents listed in "italics" are carried over from proteolysis and are not present in Binding Buffer.

Example 4—Nucleic Acid Capture by Glass Fiber Vacuum Filtration

Prepare glass fiber spin columns for filtration by labeling and fitting a disposable plastic vacuum connector to the exit port. The connectors prevent spin column contamination from the vacuum manifold. Install spin columns on the vacuum manifold and check that all connections are secure. Plug any unused vacuum ports and connect vacuum lines to the manifold and keep the pressure at zero mBar. Wet each column by carefully pipetting 500 μL of Spin Column Conditioning Solution onto the center of each membrane without directly contacting the membrane with the pipette tip. Engage the vacuum briefly to initiate a slow flow of the conditioning solution through the columns. Once complete, interrupt the vacuum. Attach a 45 mL Column Extender to each column and check to make sure the connections are snug. Initiate NA binding by carefully pouring plasma lysates in the nucleic acid binding state into reservoir extenders and initiate filtration by bringing the vacuum to −600 to −800 mBar. Filtration times may vary from sample to sample, but should complete within 45 minutes, and not typically less than 10 minutes. Wash both columns as described below and elute sequentially with 55 uL elution buffer passed over first one column and then the next, recovering the eluate in a single tube.

Example 5—Sequential Wash Steps, Residual Wash Removal and Drying

Once filtration of all plasma binding lysates is complete, remove the reservoir extender from each spin column, and add 850 uL of Wash Buffer 1 to each spin column. Release the vacuum, bring the pressure to 0 mBar, and add 825 μL of Wash Buffer 2 and reengage the vacuum to draw wash buffer through column. Turn off the vacuum and allow the pressure to reach 0 mbar and add 825 uL of 100% ethanol resume filtration under a vacuum of −600 mBar. Once filtration is complete, allow columns to dry under vacuum for 1 minute, then deduce the vacuum pressure to 0 mBar and close the lid of each spin column. Take each column off the vacuum manifold, remove the disposable vacuum connectors, and place each into a clean 2.0 mL collection tube. Load into a microcentrifuge and spin at 14,000 rpm for 3 minutes to dry residual EtOH. Preheat Elution Buffer to 56° C. prior to elution. Transfer each spin column to a 1.5 mL pre-labeled LoBind microcentrifuge tube.

Example 6—NA Elution from Glass Fiber Spin Columns

Add 50 uL of pre-heated Elution Buffer to the center of each filter without touching the filter membrane with the pipette tip. Close spin column lids and incubate at room temperature (18° C. to 22° C.) for 7-10 minutes. Elute cfDNA by centrifugation at 14,000 rpm for 1 minute. Recovered cfDNA can be taken directly into NGS library preparation or stored at −20° C. for future analysis.

Example 7—Comparative Testing

As shown in FIG. 1, when IPA was used as solvent, recovery of short dsDNA increased as the IPA concentration was raised and the GnCl concentration fell due to volume displaced by the added solvent.

Figure 2:
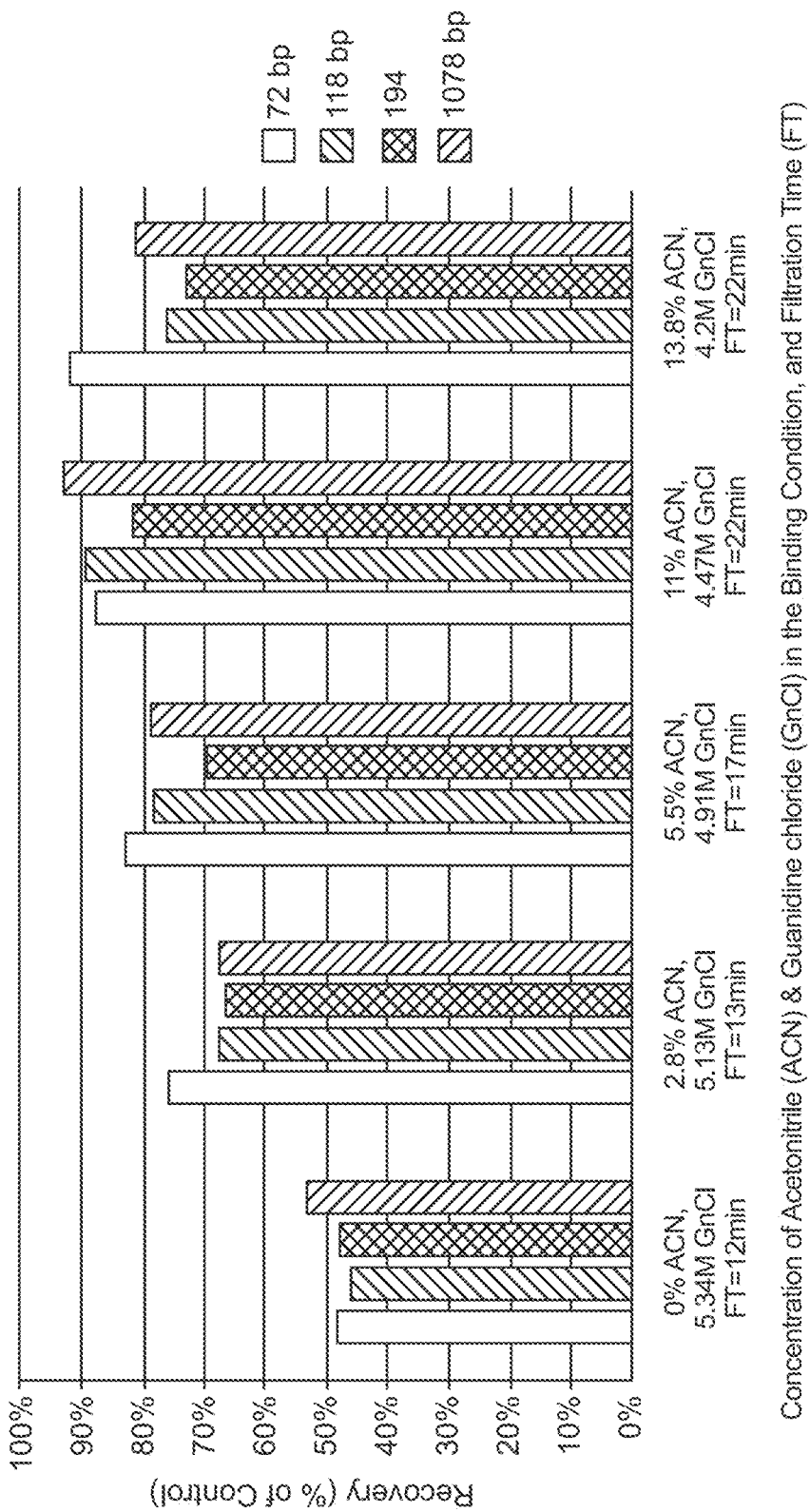
FIG. 2 shows recovery of DNA as a function of the concentration of acetonitrile (ACN) and GnCl in the nucleic acid binding state. Recovery of short dsDNA increases as the ACN concentration is raised and GnCl concentrations fall due to volume displaced by the added solvent. Exogenous DNA targets spiked following proteolysis were quantified by real time PCR quantified using standard curve methods. The percent recovery for each target was determined by comparison against recovery controls assembled by adding the original spike amount to eluates recovered from matched plasma samples isolated with a similar test chemistry. Test samples were normalized with buffer to account for spike volumes added to recovery controls.

As shown in FIG. 2, when ACN was used as solvent, recovery of short dsDNA increased as the ACN concentration was raised and the GnCl concentration fell due to volume displaced by the added solvent.

Figure 3:
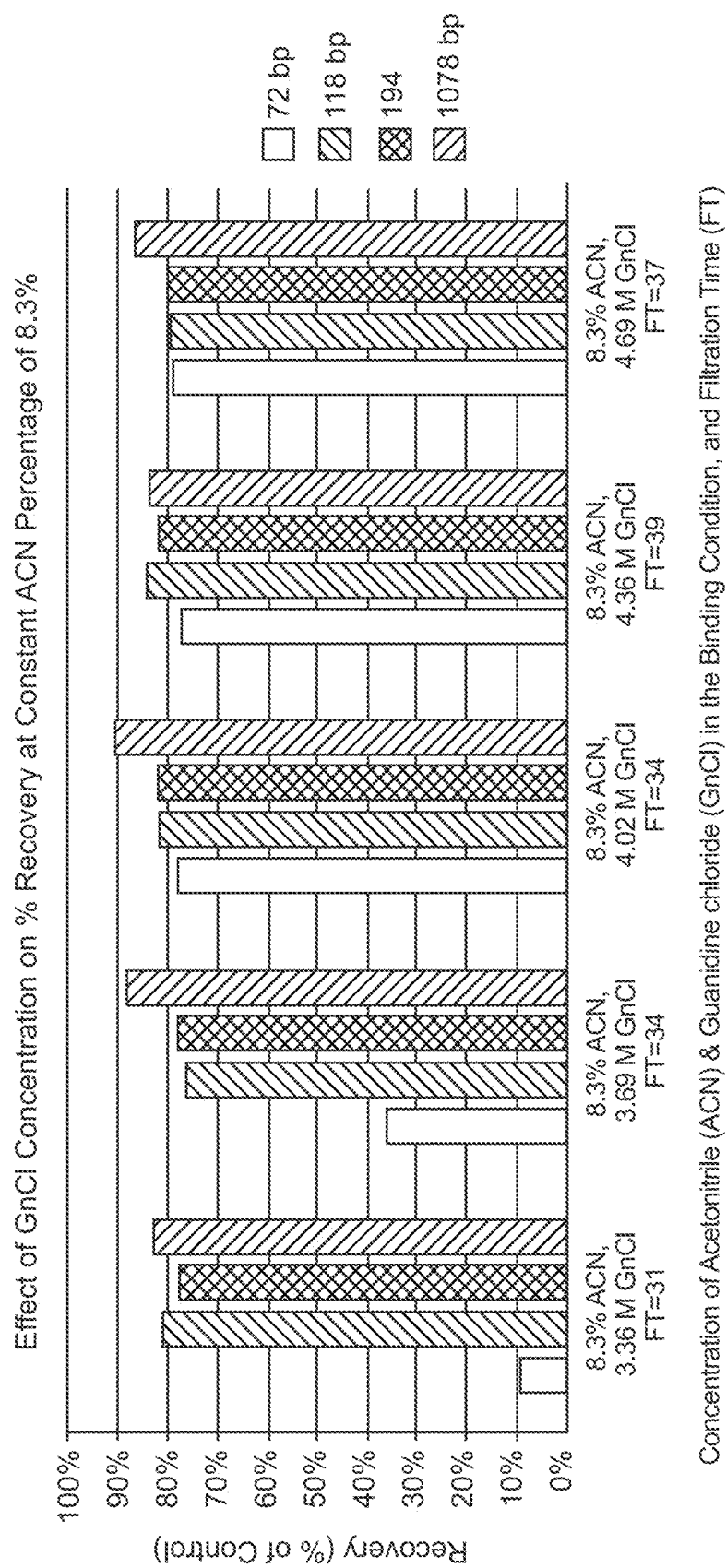
FIG. 3 shows recovery of DNA as a function of GnCl concentration in the nucleic acid binding state when ACN was held constant at 8.3%. Recovery of short dsDNA increased as the concentration of GnCl was increased relative to a constant amount of ACN. Exogenous DNA targets were spiked following proteolysis and quantified by real time PCR and standard curve methods. The percent recovery of each target fragment was calculated by comparing against spike controls in which the original spike amount was added to eluates recovered from matched plasma samples. All test samples were normalized with buffer to account for spike volumes added to recovery controls.

As shown in FIG. 3, recovery of short dsDNA increased as the concentration of GnCl was increased relative to a constant amount of ACN (8.3% ACN in the NA binding state).

Figure 4:
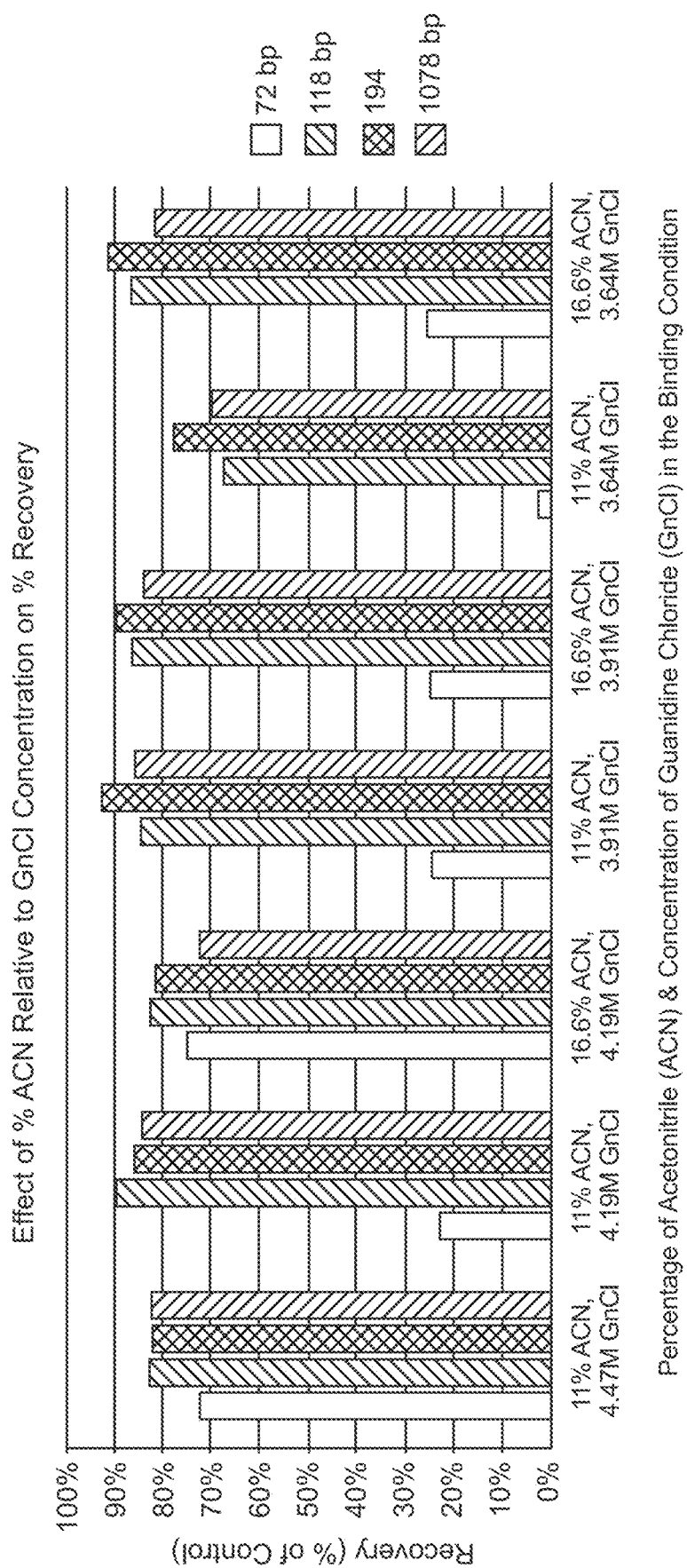
FIG. 4 shows recovery of DNA as a function of the relative amount of ACN and GnCl in the nucleic acid binding state. Recovery of short dsDNA decreased as the concentration of GnCl or percentage of ACN was reduced in the nucleic acid binding state. An increase of either ACN or GnCl compensated for the deficiency of the other. For instance, recovery of the 72 bp fragment improved when ACN was held constant at 11% and GnCl increased from 4.19 M to 4.47 M. This also happened when GnCl was held constant at 4.19 M and ACN increased from 11% to 16.6%. Exogenous DNA targets were spiked following proteolysis and quantified by real time PCR using standard curve methods. Percent recovery for each fragment was determined by comparison to spike controls established by adding the original spike amount to eluted cfDNA isolated from plasma samples by a similar test method. All test samples were normalized with buffer to account for the volume added to recovery controls.

As shown in FIG. 4, recovery of short dsDNA decreased as the concentration of GnCl or percentage of ACN was reduced. An increase of either ACN or GnCl can compensate for the insufficiency of the other. For instance, recovery of the 72 bp and 118 bp fragment improved when ACN was held constant at 11% and GnCl was increased from 4.19 M to 4.47 M, and also when GnCl was held constant at 4.19 M and ACN was increased from 11% to 16.6% in the nucleic acid binding state.

Figure 5:
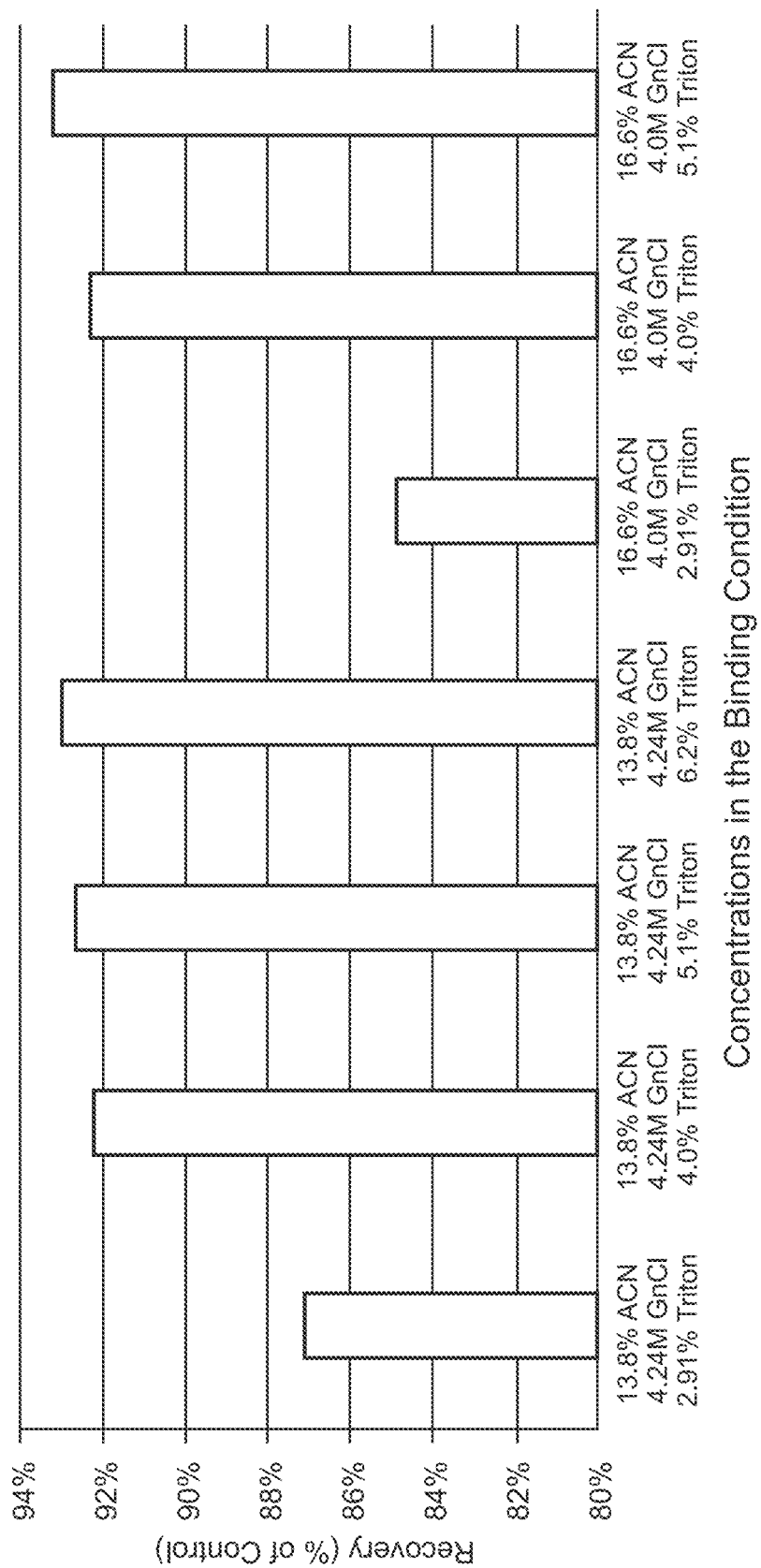
FIG. 5 shows recovery of DNA with increasing amount of Triton X100 in the nucleic acid binding state. Increased concentration of Triton yielded an increase in spike recovery of the 72 bp exogenous DNA target. Targets were quantified by real time PCR using standard curve methods. Percent recovery was determined by comparison against spike controls generated by adding spike targets to eluted cfDNA isolated from plasma samples by a similar test method. All test samples were normalized with buffer to account for the addition of spike material to recovery controls.

As shown in FIG. 5, increased concentration of Triton in the binding condition yielded an increase in spike recovery of the 72 bp exogenous DNA target, under two different test conditions (13.8% ACN and 4.24 M GnCl, or 16.6% ACN and 4 M GnCl).

Figure 6:
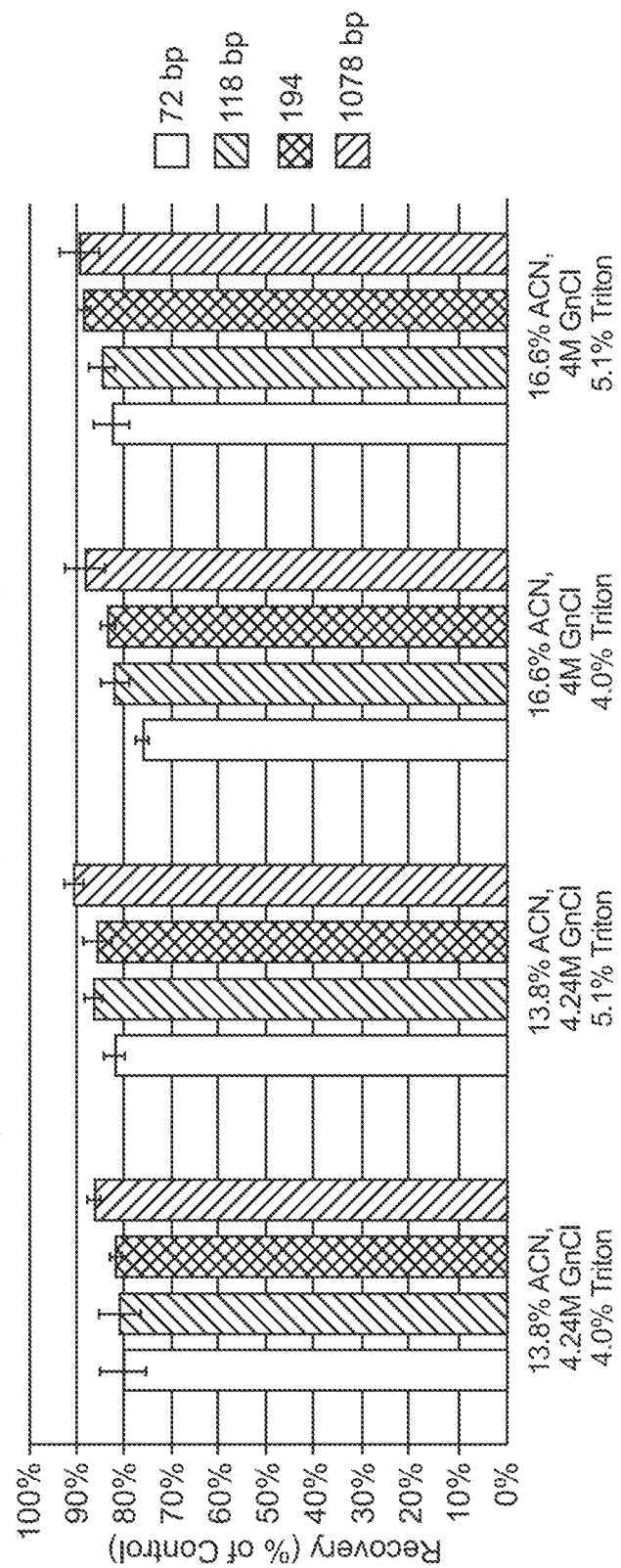
FIG. 6 shows recovery of DNA from 2 extractions from 2 single donor plasma samples (N=4). The amount of Triton X100 in the nucleic acid binding state was varied to reveal an overall increase in spike recovery with increased Triton at two different ACN and GnCl concentrations in the nucleic acid binding state. Exogenous DNA targets spiked following proteolysis were quantified by real time PCR using standard curve methods. Percent recovery for each target fragment was determined by comparison against the original amount of spike target added to recovered plasma cfDNA extracted by a similar test method. All test samples were normalized with buffer to account for the addition of spike material to recovery controls.

As shown in FIG. 6, increased concentration of Triton in the binding condition yielded an increase in recovery of small DNA fragments from 2 single donor plasma samples under two different test conditions (13.8% ACN and 4.24 M GnCl, or 16.6% ACN and 4 M GnCl).

Figure 7:
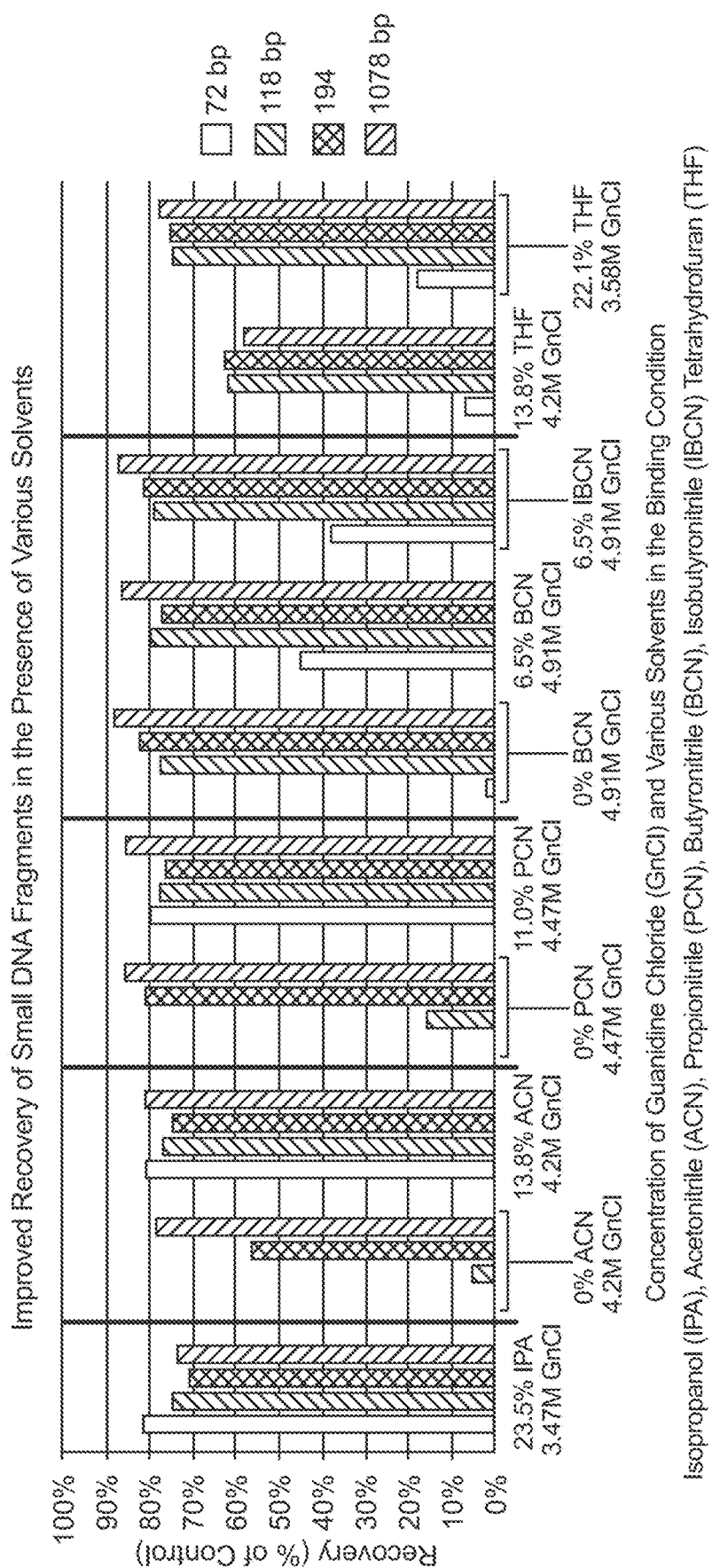
FIG. 7 shows recovery of DNA as a function of organic solvent used to establish the nucleic acid binding state. Various water soluble solvents were added to create the binding condition, and surprisingly it was revealed that solvents whose results are presented (ACN, PCN, BCN, MCN and THF) all promoted an increase in recovery of the 72 bp and 118 bp fragments compared to the 0% controls (series 2, 4 and 6) in which solvent was replaced by water. Exogenous DNA targets spiked following proteolysis were quantified by real time PCR using standard curve methods. Percent recovery for each target fragment was determined by comparison against the original amount of spike target added to recovered plasma cfDNA extracted by a similar test method. All test samples were normalized with buffer to account for the addition of spike material to recovery controls.

As shown in FIG. 7, various water soluble solvents other than ACN were added to create binding conditions that could promote increased recovery of the 72 bp DNA fragment.

As shown in FIG. 9, fetal fraction estimates for matched pair pregnancy samples were significantly increased when cfDNA was isolated when ACN served as a co-solvent in comparison to IPA in the nucleic acid binding state.

Figure 10:
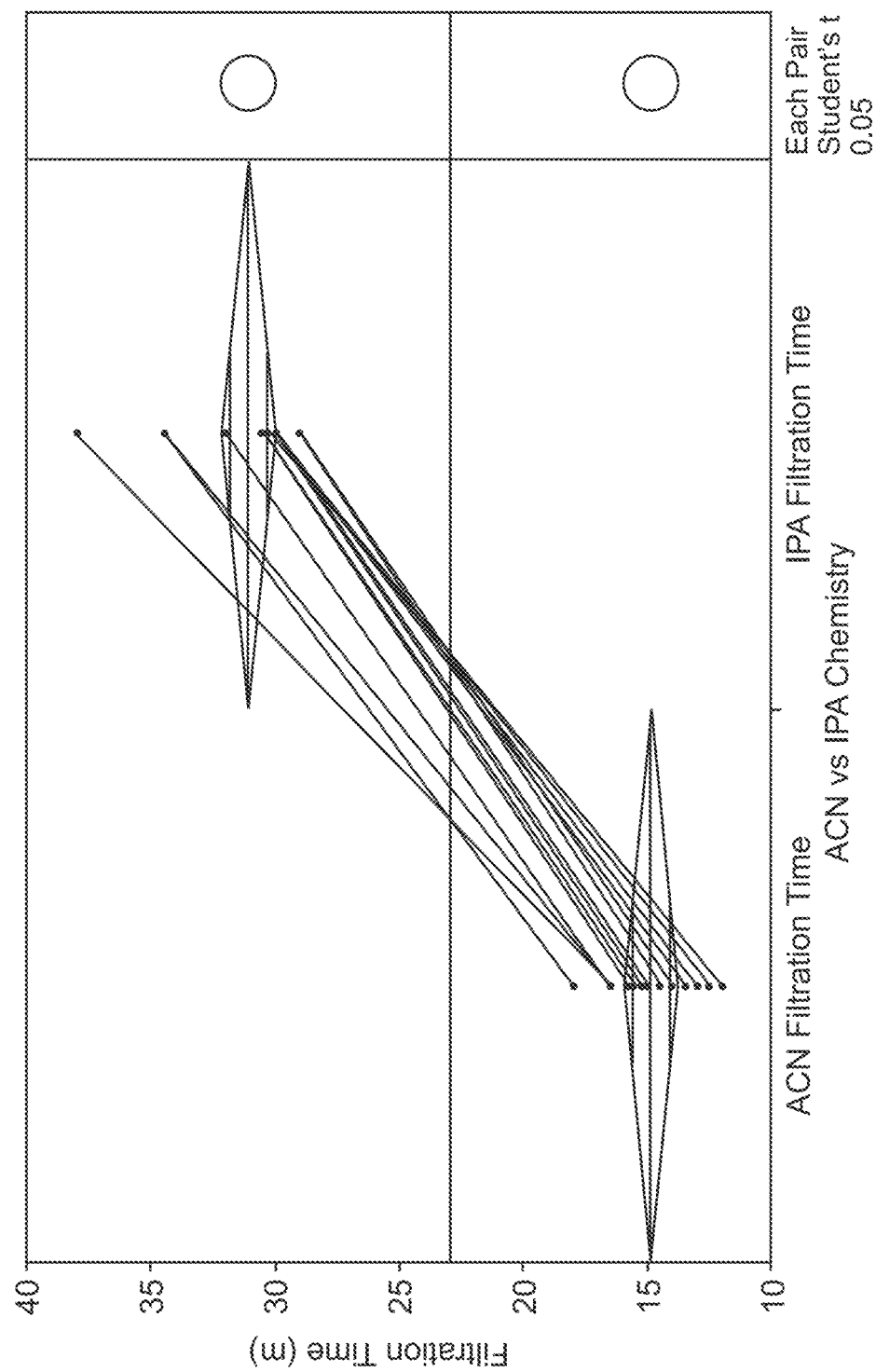
FIG. 10 presents a one-way analysis of variance showing decreased filtration times for plasma cfDNA extractions for which the binding state was established with acetonitrile (ACN) and compared directly to isopropyl alcohol (IPA). The pairwise comparison is of 16 plasma samples from maternal donors isolated by two different optimized methods, one utilizing acetonitrile (ACN) and one isopropyl alcohol (IPA) to establish the nucleic acid binding state (Refer to FIGS. 1 and 2 for a comparison of yield of fragments of various size). Mean filtration times were much shorter when the aprotic solvent ACN was used.
Figure 11:
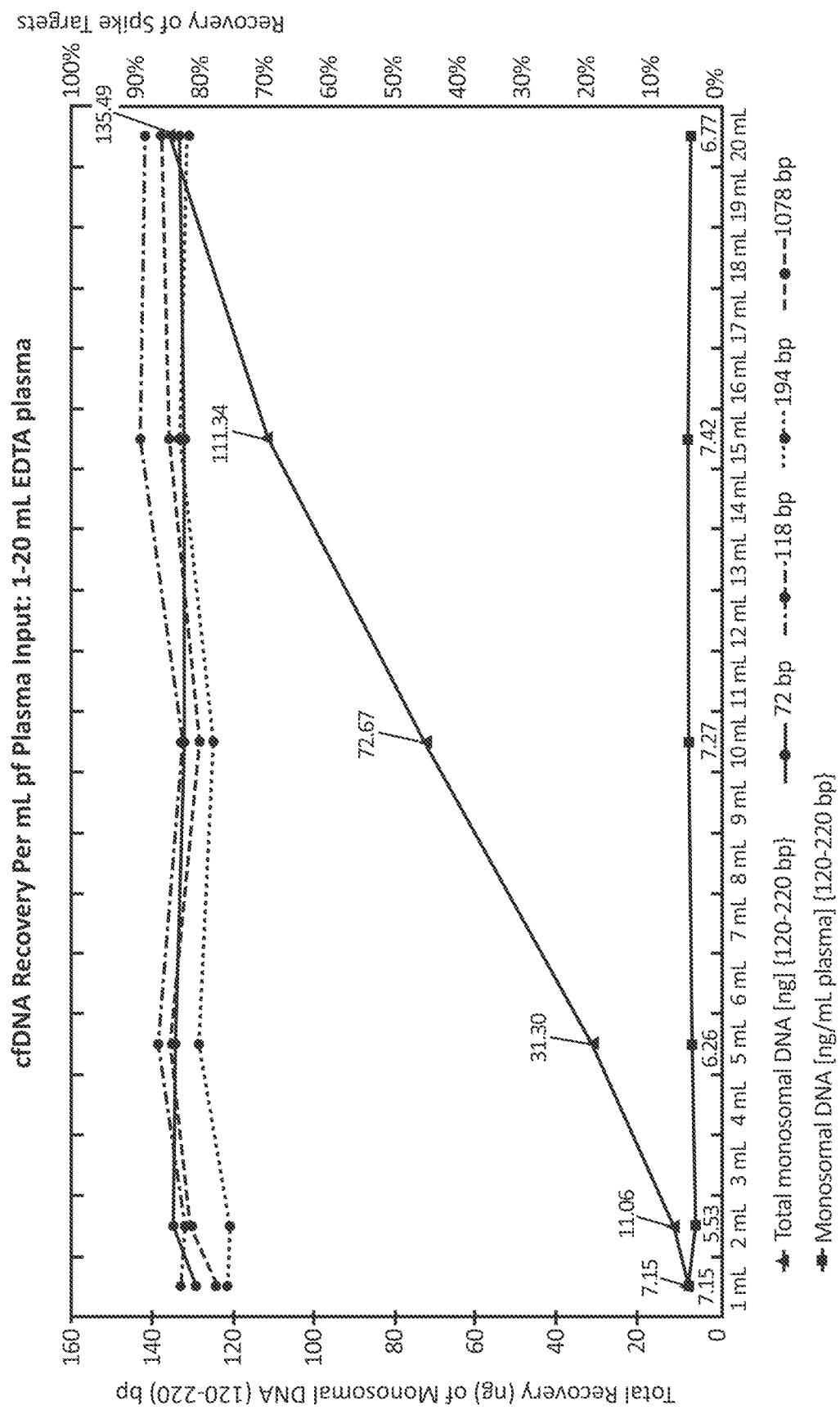
FIG. 11 shows extraction linearity. The plot summarized the total yield of cfDNA and % recovery of the 72, 118, 194 and 1078 bp spike targets from varying input amounts of human plasma. Human plasma; 1, 2, 5, 10, 15 and 20 mL were used as input. The 1 to 5 mL plasma samples were normalized to 10 mL with the addition of 1×PBS and extracted, along with the 10 mL plasma sample, by the standard 10 mL plasma NAS protocol. Reagent volumes were increased proportionally for the 15 and 20 mL plasma samples. 200 pg of spike target mixture was added to each normalized plasma and recovery, as a % of control, was determined by qPCR. Recovery of cfDNA was estimated from Caliper LabChip CE traces by quantifying DNA between 120 and 220 bp (i.e., mono-nucleosome in size). The results show that DNA extraction efficiency is consistent across all plasma volumes. This is shown in the upper portion of the plot by the clustering of recovery data for all four DNA fragment, which returned 80 to 92% of the original spike amount (right axis), for the 72 bp (solid line), 118 bp (dot-dash-dot), 194 bp (dotted line), and 1078 bp (dashed line), respectively. Recovery of monosomal cfDNA scaled linearly with plasma volume input, and correspondingly, the recovery per mL of plasma was constant from 1 to 20 mL of plasma, demonstrating that this method is scalable and efficient across a broad range of input.
Figure 12:
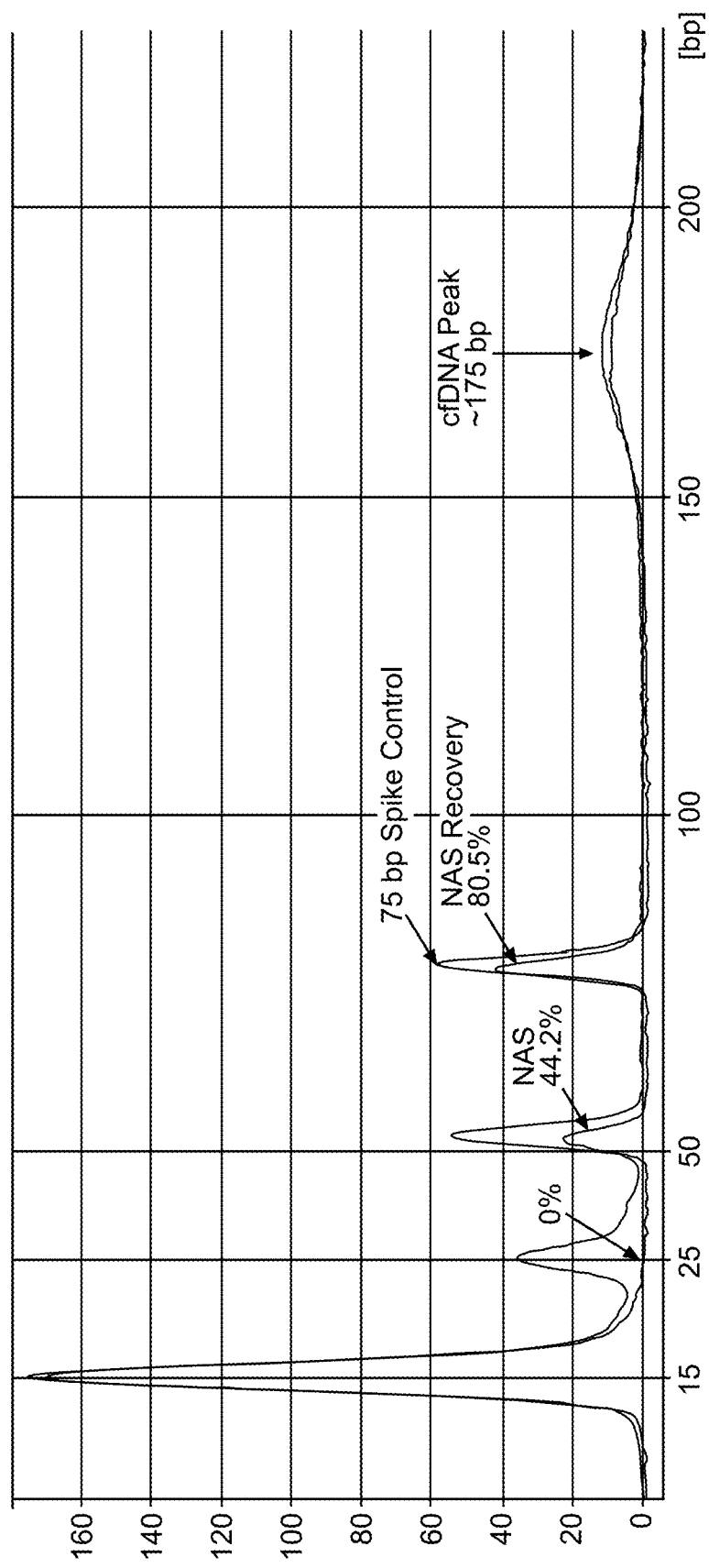
FIG. 12 shows extraction recovery of 25 bp, 50 bp and 75 bp dsDNA fragments from plasma. A mixture of these dsDNA spike fragments was added to a 10 mL Test plasma sample, and buffer only to a matched 10 mL plasma to serve as Control. The NAS extraction method was carried out on both samples. An equivalent amount of spike fragments were added eluted cfDNA from the Control and the same amount of buffer to the Test eluate. 1 uL of each eluate was separated by capillary electrophoresis on an Agilent Bioanalyzer HS chip and the fluorescence plots for each run were overlayed. The plot of the Control run shows three of the tallest peaks at 25, 50 and 75 bp. The plot of lower amplitude shows that 80.5% and 44.2% of the 75 and 50 bp fragments, respectively, were recovered from 10 mL plasma by the NAS extraction method. None of the 25 bp fragment, however, was recovered. This suggests that the NAS chemistry is capable of recovering fragments as small as 50 bp with reasonable efficiency, and fragments of 75 bp in length with good efficiency, in agreement with the qPCR results shown in other figures.

As shown in FIG. 10, filtration times through glass fiber filters were significantly shorter for match paired plasma samples when the nucleic acid binding state was established with ACN as a co-solvent compared to IPA.

Additional Embodiments

Embodiment 1

A composition for isolating nucleic acids from a biological sample, comprising a chaotropic compound and a solvent, wherein the solvent comprises a nitrile compound, tetrahydrofuran (THF), or a combination thereof.

Embodiment 2

The composition of Embodiment 1, wherein the nitrile compound is acetonitrile (ACN), propionitrile (PCN), butyronitrile (BCN), isobutylnitrile (IBCN), or a combination thereof.

Embodiment 3

The composition of Embodiment 1, wherein the nitrile compound is ACN.

Embodiment 4

The composition of Embodiment 3, wherein the composition comprises about 10% to about 20% of ACN.

Embodiment 5

The composition of Embodiment 3, wherein the composition comprises about 13% to about 18% of ACN.

Embodiment 6

The composition of Embodiment 3, wherein the composition comprises about 15% of ACN.

Embodiment 7

The composition of any of Embodiments 1-6, wherein pH of the composition is about 4 to about 8.

Embodiment 8

The composition of Embodiment 7, wherein pH of the composition is about 4.9 to about 5.1.

Embodiment 9

The composition of any of Embodiments 1-8, wherein the chaotropic compound is guanidine chloride (GnCl), urea, thiourea, guanidine thiocyanate, NaI, guanidine isothiocyanate, D-/L-arginine, a perchlorate or perchlorate salt of Li+, Na+, K+, or a combination thereof.

Embodiment 10

The composition of Embodiment 9, wherein the chaotropic compound is GnCl.

Embodiment 11

The composition of Embodiment 10, wherein the concentration of GnCl is about 3.5 M to about 6 M.

Embodiment 12

The composition of Embodiment 10, wherein the concentration of GnCl is about 4 M to about 5 M.

Embodiment 13

The composition of Embodiment 10, wherein the concentration of GnCl is about 4.4 M.

Embodiment 14

The composition of any of Embodiments 1-13, further comprises a chelating compound.

Embodiment 15

The composition of Embodiment 14, wherein the chelating compound is ethylenediaminetetraccetic (EDTA), ethyleneglycol-bis(2-aminoethylether)-N,N,N',N'-tetraacetic acid (EGTA), citric acid, N,N,N',N'-Tetrakis(2-pyridylmethyl)ethylenediamine (TPEN), 2,2'-Bipyridyl, deferoxamine methanesulfonate salt (DFOM), 2,3-Dihydroxybutanedioic acid (tartaric acid), or a combination thereof.

Embodiment 16

The composition of any of Embodiments 1-15, further comprises a detergent.

Embodiment 17

The composition of Embodiment 16, wherein the detergent is Triton X-100, Tween 20, N-lauroyl sarcosine, sodium dodecylsulfate (SDS), dodecyldimethylphosphine oxide, sorbitan monopalmitate, decylhexaglycol, 4-nonylphenyl-polyethylene glycol, or a combination thereof.

Embodiment 18

The composition of Embodiment 17, wherein the detergent is Triton X-100.

Embodiment 19

The composition of Embodiment 18, wherein the composition comprises about 3% to about 6% of Triton X-100.

Embodiment 20

The composition of Embodiment 18, wherein the composition comprises about 4% to about 5% of Triton X-100.

Embodiment 21

The composition of Embodiment 18, wherein the composition comprises about 4.5% of Triton X-100.

Embodiment 22

The composition of any of Embodiments 1-21, further comprises nucleic acids.

Embodiment 23

The composition of Embodiment 22, wherein the nucleic acids are cell free nucleic acids or circuiting tumor nucleic acids.

Embodiment 24

The composition of Embodiment 23, wherein the cell free nucleic acids are obtained from a sample of a maternal blood, plasma, or serum.

Embodiment 25

The composition of Embodiment 24, wherein the cell free nucleic acids comprise cell free fetal DNA and cell free maternal DNA.

Embodiment 26

The composition of Embodiment 22, wherein the nucleic acids are maternal nucleic acids or fetal nucleic acids.

Embodiment 27

The composition of any of Embodiments 22-26, wherein the nucleic acids are about 50 to about 1200 base pairs in length.

Embodiment 28

The composition of any of Embodiments 22-27, wherein the nucleic acids are about 70 to about 500 base pairs in length.

Embodiment 29

The composition of any of Embodiments 22-28, wherein the nucleic acids are about 100 to about 200 base pairs in length.

Embodiment 30

The composition of any of Embodiments 22-29, wherein the nucleic acids are about 130 to about 170 base pairs in length.

Embodiment 31

The composition of any of Embodiments 22-30, wherein the nucleic acids are DNAs or RNAs.

Embodiment 32

The composition of Embodiment 31, wherein the nucleic acids are DNAs.

Embodiment 33

The composition of Embodiment 1, further comprises a matrix.

Embodiment 34

The composition of Embodiment 33, wherein the matrix comprises siliceous materials, silica gel, glass, glass fiber, zeolite, aluminum oxide, titanium dioxide, zirconium dioxide, kaolin, gelatinous silica, magnetic particles, ceramics, polymeric supporting materials, and or a combination thereof.

Embodiment 35

The composition of Embodiment 34, wherein the matrix comprises glass fiber.

Embodiment 36

A method for binding nucleic acids to a matrix, comprising: contacting the nucleic acids from a biological sample with the matrix in the presence of a chaotropic compound and a solvent, wherein the solvent comprises a nitrile compound, tetrahydrofuran (THF), or a combination thereof, thereby binding the nucleic acids to the matrix.

Embodiment 37

The method of Embodiment 36, wherein the nitrile compound is ACN.

Embodiment 38

The method of Embodiment 37, wherein the nucleic acids are contacted with the matrix in the presence of about 10% to about 20% of ACN.

Embodiment 39

The method of Embodiment 37, wherein the nucleic acids are contacted with the matrix in the presence of about 13% to about 18% of ACN.

Embodiment 40

The method of Embodiment 37, wherein the nucleic acids are contacted with the matrix in the presence of about 15% of ACN.

Embodiment 41

The method of any of Embodiments 36-40, wherein the chaotropic compound is GnCl.

Embodiment 42

The method of Embodiment 41, wherein the nucleic acids are contacted with the matrix in the presence of about 3.5 M to about 6 M of GnCl.

Embodiment 43

The method of Embodiment 41, wherein the nucleic acids are contacted with the matrix in the presence of about 4 M to about 5 M of GnCl.

Embodiment 44

The method of Embodiment 41, wherein the nucleic acids are contacted with the matrix in the presence of about 4.4 M of GnCl.

Embodiment 45

The method of any of Embodiments 36-44, wherein the nucleic acids are contacted with the matrix also in the presence of a chelating compound.

Embodiment 46

The method of Embodiment 45, wherein the chelating compound is EDTA, EGTA, citric acid, TPEN, 2,2'-Bipyridyl, DFOM, tartaric acid, or a combination thereof.

Embodiment 47

The method of any of Embodiments 36-46, wherein the nucleic acids are contacted with the matrix also in the presence of a detergent.

Embodiment 48

The method of Embodiment 47, wherein the detergent is Triton X-100, Tween 20, N-lauroyl sarcosine, SDS, dodecyldimethylphosphine oxide, sorbitan monopalmitate, decylhexaglycol, 4-nonylphenyl-polyethylene glycol, or a combination thereof.

Embodiment 49

The method of Embodiment 48, wherein the detergent is Triton X-100.

Embodiment 50

The method of Embodiment 49, wherein the nucleic acids are contacted with the matrix in the presence of about 3% to about 6% of Triton X-100.

Embodiment 51

The method of Embodiment 49, wherein the nucleic acids are contacted with the matrix in the presence of about 4% to about 5% of Triton X-100.

Embodiment 52

The method of Embodiment 49, wherein the nucleic acids are contacted with the matrix in the presence of about 4.5% of Triton X-100.

Embodiment 53

The method of any of Embodiments 36-52, wherein the nucleic acids are cell free nucleic acids or circuiting tumor nucleic acids.

Embodiment 54

The method of Embodiment 53, wherein the cell free nucleic acids are obtained from a sample of a maternal blood, plasma, or serum.

Embodiment 55

The method of Embodiment 54, wherein the cell free nucleic acids comprise cell free fetal DNA and cell free maternal DNA.

Embodiment 56

The method of any of Embodiments 36-52, wherein the nucleic acids are maternal nucleic acids or fetal nucleic acids.

Embodiment 57

The method of any of Embodiments 36-56, wherein the nucleic acids are about 50 to about 1200 base pairs in length.

Embodiment 58

The method of any of Embodiments 36-57, wherein the nucleic acids are about 70 to about 500 base pairs in length.

Embodiment 59

The method of any of Embodiments 36-58, wherein the nucleic acids are about 100 to about 200 base pairs in length.

Embodiment 60

The method of any of Embodiments 36-59, wherein the nucleic acids are about 130 to about 170 base pairs in length.

Embodiment 61

The method of any of Embodiments 36-60, wherein the nucleic acids are DNAs or RNAs.

Embodiment 62

The method of Embodiment 61, wherein the nucleic acids are DNAs.

Embodiment 63

The method of any of Embodiments 36-62, wherein the matrix comprises siliceous materials, silica gel, glass, glass fiber, zeolite, aluminum oxide, titanium dioxide, zirconium dioxide, kaolin, gelatinous silica, magnetic particles, ceramics, polymeric supporting materials, or a combination thereof.

Embodiment 64

The method of Embodiment 63, wherein the matrix comprises glass fiber.

Embodiment 65

The method of any of Embodiments 36-64, further comprises incubating a biological sample comprising the nucleic acids with a protease prior to contacting the nucleic acids with the matrix.

Embodiment 66

The method of Embodiment 65, wherein the biological sample is a sample of a maternal blood, plasma, or serum.

Embodiment 67

The method of any of Embodiments 36-66, further comprises washing the matrix with a washing buffer.

Embodiment 68

The method of any of Embodiments 36-67, further comprises drying the matrix.

Embodiment 69

The method of any of Embodiments 36-68, further comprises eluting the nucleic acids from the matrix with an elution buffer.

Embodiment 70

A kit for isolating nucleic acids from a biological sample, comprising a binding buffer, wherein the binding buffer comprises a chaotropic compound and a solvent, wherein the solvent comprises a nitrile compound, tetrahydrofuran (THF), or a combination thereof.

Embodiment 71

The kit of Embodiment 70, wherein the nitrile compound is ACN.

Embodiment 72

The kit of Embodiment 71, wherein the binding buffer comprises about 15% to about 35% of ACN.

Embodiment 73

The kit of Embodiment 71, wherein the binding buffer comprises about 20% to about 30% of ACN.

Embodiment 74

The kit of Embodiment 71, wherein the binding buffer comprises about 25% of ACN.

Embodiment 75

The kit of any of Embodiments 70-74, wherein the chaotropic compound in binding buffer is GnCl.

Embodiment 76

The kit of Embodiment 75, wherein the concentration of GnCl in binding buffer is about 5 M to about 8 M.

Embodiment 77

The kit of Embodiment 75, wherein the concentration of GnCl in binding buffer is about 5.6 M to about 7.2 M.

Embodiment 78

The kit of Embodiment 75, wherein the concentration of GnCl in binding buffer is about 6 M.

Embodiment 79

The kit of any of Embodiments 70-78, wherein the binding buffer further comprises a chelating compound.

Embodiment 80

The kit of Embodiment 79, wherein the chelating compound is EDTA, EGTA, citric acid, TPEN, 2,2'-Bipyridyl, DFOM, tartaric acid, or a combination thereof.

Embodiment 81

The kit of any of Embodiments 70-80, wherein the binding buffer further comprises a detergent.

Embodiment 82

The kit of Embodiment 81, wherein the detergent is Triton X-100, Tween 20, N-lauroyl sarcosine, SDS, dodecyldimethylphosphine oxide, sorbitan monopalmitate, decylhexaglycol, 4-nonylphenyl-polyethylene glycol, or a combination thereof.

Embodiment 83

The kit of Embodiment 82, wherein the detergent is Triton X-100.

Embodiment 84

The kit of Embodiment 83, wherein the binding buffer comprises about 1% to about 6% of Triton X-100.

Embodiment 85

The kit of Embodiment 83, wherein the binding buffer comprises about 2% to about 4% of Triton X-100.

Embodiment 86

The kit of Embodiment 83, wherein the binding buffer comprises about 3% of Triton X-100.

Embodiment 87

The kit of any of Embodiments 70-86, wherein the binding buffer has a pH of about 4 to about 8.

Embodiment 88

The kit of any of Embodiments 70-87, wherein the binding buffer has a pH of about 4.9 to about 5.1.

Embodiment 89

The kit of any of Embodiments 70-88, wherein the kit further comprises a digestion buffer comprising a protease.

Embodiment 90

The kit of any of Embodiments 70-89, wherein the kit further comprises a washing buffer.

Embodiment 91

The kit of any of Embodiments 70-90, wherein the kit further comprises an elution buffer.

Embodiment 92

A method for providing a binding condition for nucleic acids, comprising mixing the binding buffer of any of Embodiments 70-88 with a composition comprising a biological sample that has been pre-treated with a protease and that comprises the nucleic acids.

As used herein, the singular terms "a," "an," and "the" include plural referents unless the context clearly dictates otherwise. Thus, for example, reference to a molecule can include multiple molecules unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A composition comprising:
    a binding buffer comprising 4 M to 6 M of guanidine chloride, 10% to 20% of acetonitrile and less than 2% alcohol;
    a matrix comprising siliceous materials, silica gel, glass, glass fiber, zeolite, kaolin, gelatinous silica, or a combination thereof; and
    cell-free fetal DNA or circulating tumor DNA,
wherein at least 50% of the cell-free fetal DNA or circulating tumor DNA having a size of 72 bp is bound to the matrix.

2. The composition of claim 1, wherein the binding buffer comprises 13% to 18% of acetonitrile.

3. The composition of claim 1, wherein the pH of the binding buffer is 4 to 8.

4. The composition of claim 1, wherein the composition comprises 4 M to 5 M of guanidine chloride.

5. The composition of claim 1, wherein the binding buffer further comprises a chelating compound comprising ethylenediaminetetraccetic, ethyleneglycol-bis(2-aminoethylether)-N,N,N',N'-tetraacetic acid, citric acid, N,N,N',N'-tetrakis(2-pyridylmethyl)ethylenediamine, 2,2'-Bipyridyl, deferoxamine methanesulfonate salt, 2,3-Dihydroxybutanedioic acid, or a combination thereof.

6. The composition of claim 1, wherein the binding buffer further comprises a detergent comprising polyethylene glycol p-(1,1,3,3-tetramethylbutyl)-phenyl ether, polyoxyethylene 20 sorbitan monolaurate, N-lauroyl sarcosine, sodium dodecylsulfate, dodecyldimethylphosphine oxide, sorbitan monopalmitate, decylhexaglycol, 4-nonylphenyl-polyethylene glycol, or a combination thereof.

7. The composition of claim 6, wherein the binding buffer further comprises 3% to 6% of polyethylene glycol p-(1,1,3,3-tetramethylbutyl)-phenyl ether.

8. The composition of claim 1, wherein the composition comprises the circulating tumor DNA.

9. The composition of claim 1, wherein the composition comprises the cell-free fetal DNA and further comprises cell-free maternal DNA.

10. The composition of claim 1, wherein the binding buffer is free of isopropanol.

11. The composition of claim 1, wherein at least 70% of the cell-free fetal DNA or circulating tumor DNA having a size of 72 bp is bound to the matrix.

12. The composition of claim 1, wherein the matrix comprises glass fiber.

13. A method for binding nucleic acids to a matrix comprising:
    contacting cell-free fetal DNA or circulating tumor DNA from a biological sample with a matrix comprising siliceous materials, silica gel, glass, glass fiber, zeolite, kaolin, gelatinous silica, or a combination thereof, in the presence of a binding buffer comprising 4 M to 6 M of guanidine chloride, 10% to 20% of acetonitrile and less than 2% alcohol,
    thereby binding 50% of the cell-free fetal DNA or circulating tumor DNA having a size of 72 bp to the matrix.

14. The method of claim 13, further comprising:
    incubating a biological sample comprising cell-free fetal DNA or circulating tumor DNA with a protease prior to contacting the nucleic acids with the matrix;
    washing the matrix with a washing buffer after contacting the cell-free fetal DNA or circulating tumor DNA with the matrix;
    drying the matrix; and/or
    eluting the nucleic acids from the matrix with an elution buffer.

15. A kit for isolating nucleic acids from a biological sample, comprising:
    a binding buffer comprising 5 M to 8 M of guanidine chloride, 15% to 35% of acetonitrile, less than 2% alcohol and is free of both a nucleic acid sample and isopropanol; and
    a matrix for binding nucleic acids comprising siliceous materials, silica gel, glass, glass fiber, zeolite, kaolin, gelatinous silica, or a combination thereof.

16. The kit of claim 15, wherein the kit further comprises:
    a digestion buffer comprising a protease;
    a washing buffer; and/or
    an elution buffer.

17. The kit of claim 15, wherein the matrix comprises glass fiber.

* * * * *